United States Patent
Woodard, Jr. et al.

(10) Patent No.: US 9,913,639 B2
(45) Date of Patent: Mar. 13, 2018

(54) LAPAROSCOPIC SUTURING INSTRUMENT WITH DUAL-ACTION NEEDLE GRASPERS

(75) Inventors: James A. Woodard, Jr., Mason, OH (US); Aaron J. Brickner, Milford, OH (US); Jason R. Lesko, Harrison, OH (US)

(73) Assignee: Ethicon LLC, Guaynabo, PR (US)

( * ) Notice: Subject to any disclaimer, the term of this patent is extended or adjusted under 35 U.S.C. 154(b) by 209 days.

(21) Appl. No.: 13/419,503

(22) Filed: Mar. 14, 2012

(65) Prior Publication Data

US 2013/0245643 A1    Sep. 19, 2013

(51) Int. Cl.
  *A61B 17/04* (2006.01)
  *A61B 17/06* (2006.01)
  *A61B 17/29* (2006.01)

(52) U.S. Cl.
  CPC ...... *A61B 17/0482* (2013.01); *A61B 17/0469* (2013.01); *A61B 2017/06052* (2013.01); *A61B 2017/2936* (2013.01)

(58) Field of Classification Search
  CPC ............ A61B 17/0469; A61B 17/0482; A61B 2017/06052; A61B 2017/2936
  USPC ........................................ 606/139, 144, 148
  See application file for complete search history.

(56) References Cited

U.S. PATENT DOCUMENTS

| 5,728,113 A | 3/1998 | Sherts |
| 5,954,733 A * | 9/1999 | Yoon ............................. 606/147 |
| 5,993,466 A * | 11/1999 | Yoon ..................... A61B 17/062 606/144 |
| 6,017,358 A * | 1/2000 | Yoon ....................... A61B 17/29 600/564 |
| 6,056,771 A | 5/2000 | Proto |
| 6,071,289 A | 6/2000 | Stefanchik et al. |
| 7,588,583 B2 * | 9/2009 | Hamilton et al. ............ 606/144 |
| 7,628,796 B2 | 12/2009 | Shelton, IV et al. |
| 8,137,339 B2 | 3/2012 | Jinno et al. |
| 2008/0228204 A1 * | 9/2008 | Hamilton et al. ............ 606/148 |
| 2010/0100125 A1 | 4/2010 | Mahadevan |
| 2011/0313433 A1 | 12/2011 | Woodard, Jr. et al. |
| 2012/0123471 A1 | 5/2012 | Woodard, Jr. et al. |

(Continued)

FOREIGN PATENT DOCUMENTS

WO    WO 99/04697    2/1999

OTHER PUBLICATIONS

International Search Report and Written Opinion dated Jun. 26, 2013 for PCT/US2013/030161.

(Continued)

*Primary Examiner* — Gregory Anderson
*Assistant Examiner* — Sarah Simpson
(74) *Attorney, Agent, or Firm* — Frost Brown Todd LLC

(57) ABSTRACT

A suture needle driving instrument comprises a shaft and an end effector. The end effector is located at the distal end of the shaft and includes a pair of grasping arms. Each grasping arm comprises a respective pair of jaws. Each pair of jaws is operable to cooperate to grasp and release a suture needle. Each jaw has a needle grasping member operable to align a suture needle along a predetermined arc path. The end effector is further operable to pass the needle from one arm to the other arm during a suturing procedure. The instrument may be used through a trocar during minimally invasive surgery.

19 Claims, 29 Drawing Sheets

(56) References Cited

U.S. PATENT DOCUMENTS

2012/0143223 A1    6/2012  Woodard, Jr. et al.
2012/0150199 A1*   6/2012  Woodard et al. ............. 606/147

OTHER PUBLICATIONS

U.S. Appl. No. 61/355,832, filed Jun. 17, 2010.
U.S. Appl. No. 61/413,680, filed Nov. 15, 2010.

* cited by examiner

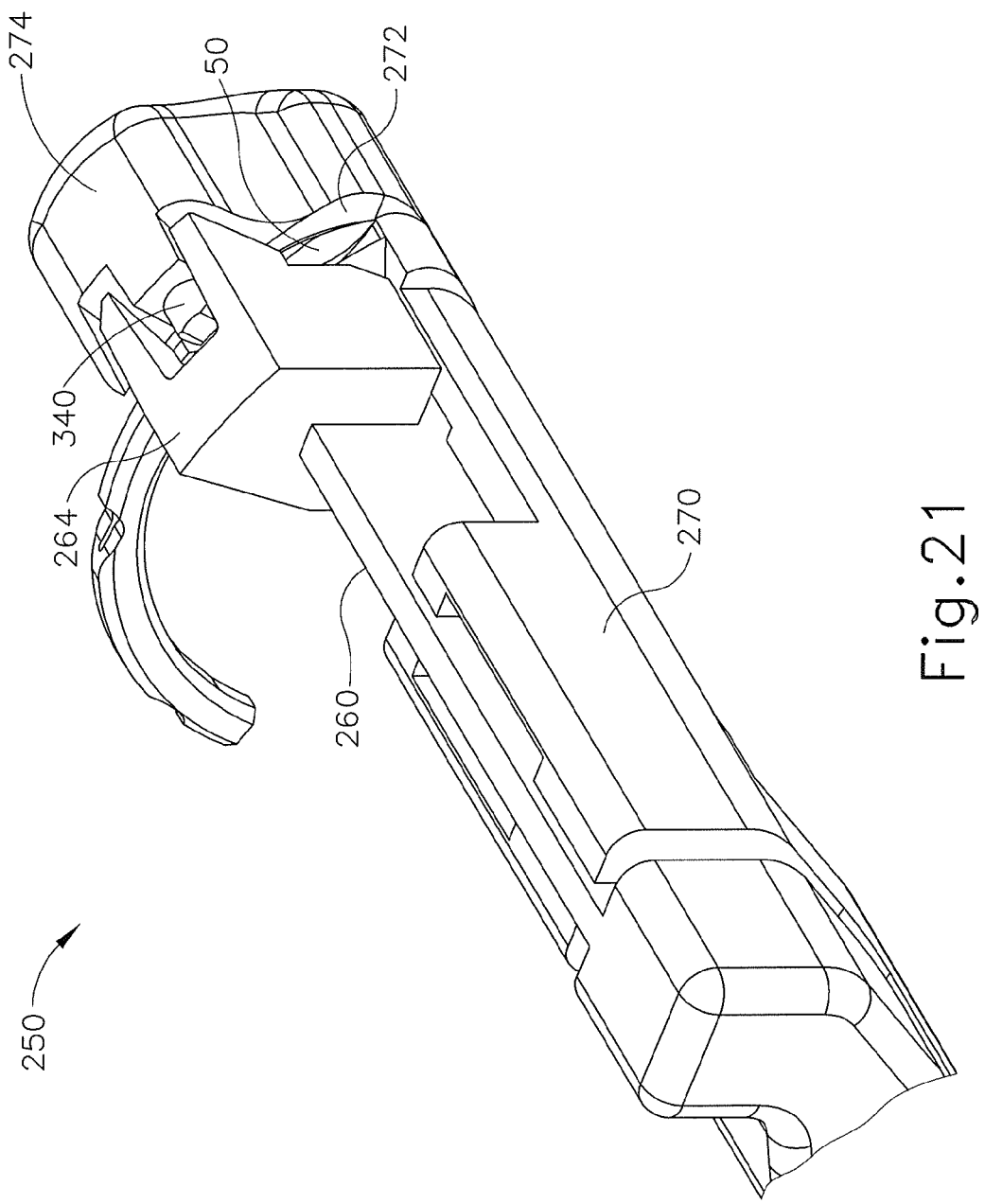

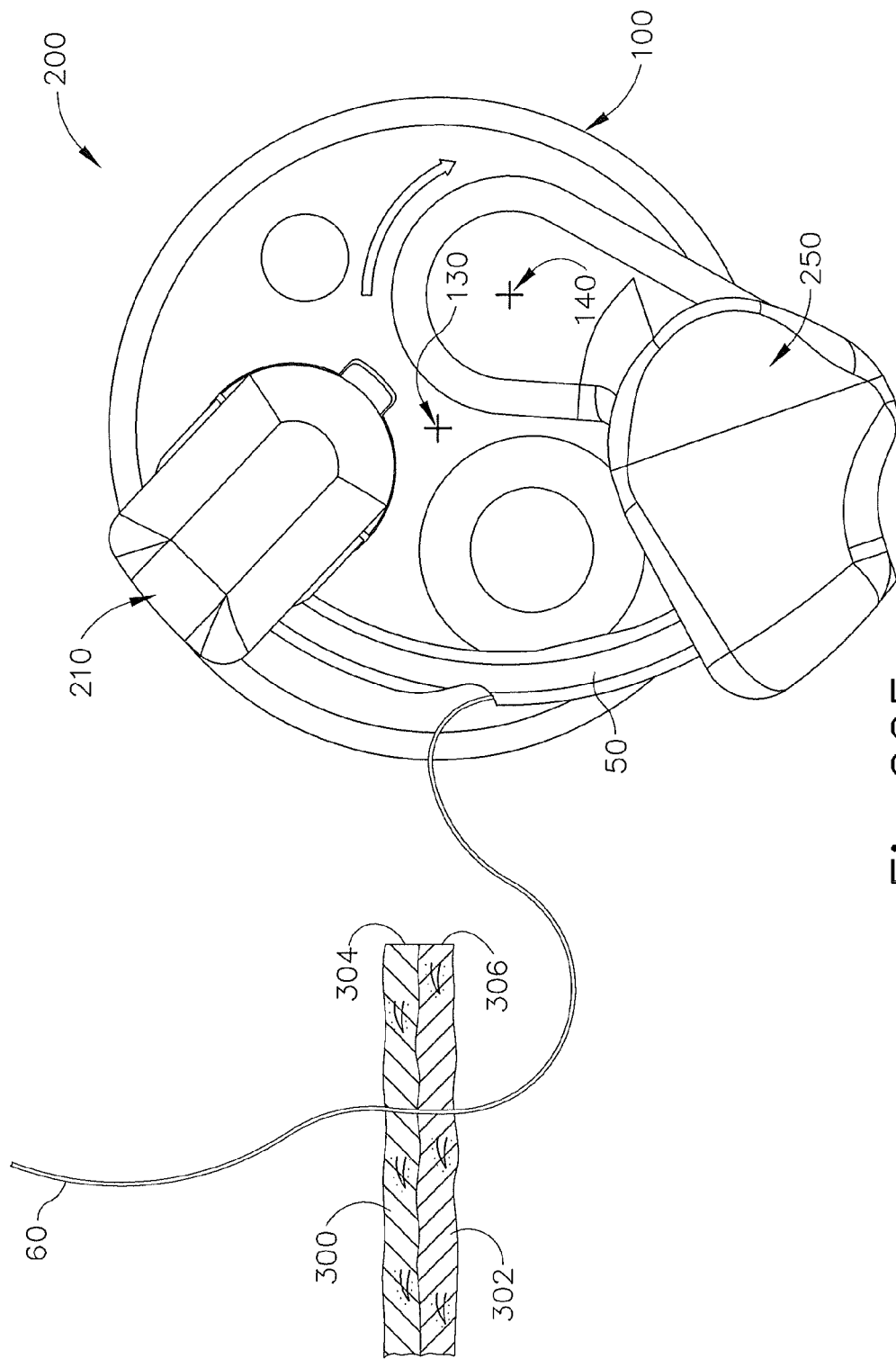

LAPAROSCOPIC SUTURING INSTRUMENT WITH DUAL-ACTION NEEDLE GRASPERS

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparascopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio. Additional suturing instruments are disclosed in U.S. Pat. No. 7,628,796, entitled "Surgical Suturing Apparatus with Anti-Backup System," issued Dec. 8, 2009, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. patent application Ser. No. 13/156,420, entitled "Laparoscopic Suture Device with Asynchronous In-Line Needle Movement," filed Jun. 9, 2011, now U.S. Pat. No. 9,168,037, issued Oct. 27, 2015, the disclosure of which is incorporated by reference herein; U.S. Provisional Patent Application No. 61/355,832, entitled "Laparoscopic Suture Device," filed Jun. 17, 2010, the disclosure of which is incorporated by reference herein; and U.S. patent application Ser. No. 13/295,210, entitled "Laparoscopic Suturing Instrument with Perpendicular Eccentric Needle Motion," filed Nov. 14, 2011, now U.S. Pat. No. 8,906,043, issued Dec. 9, 2014, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, the disclosure of which is incorporated by reference herein; U.S. Provisional Application Ser. No. 61/413,680, filed Nov. 15, 2010, entitled "Custom Needle for Suture Instrument," the disclosure of which is incorporated by reference herein; and U.S. patent application Ser. No. 13/295,186, entitled "Needle for Laparoscopic Suturing Instrument," filed on Nov. 14, 2011, now U.S. Pat. No. 9,125,646, issued Sep. 8, 2015, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 21 depicts a partial perspective view of the second needle grasping arm of FIG. 13 in a closed position grasping the needle of FIG. 2;

FIG. 22F depicts an end view of the end effector and needle of FIG. 4A, during an exemplary sixth stage of operation;

Figure 1:
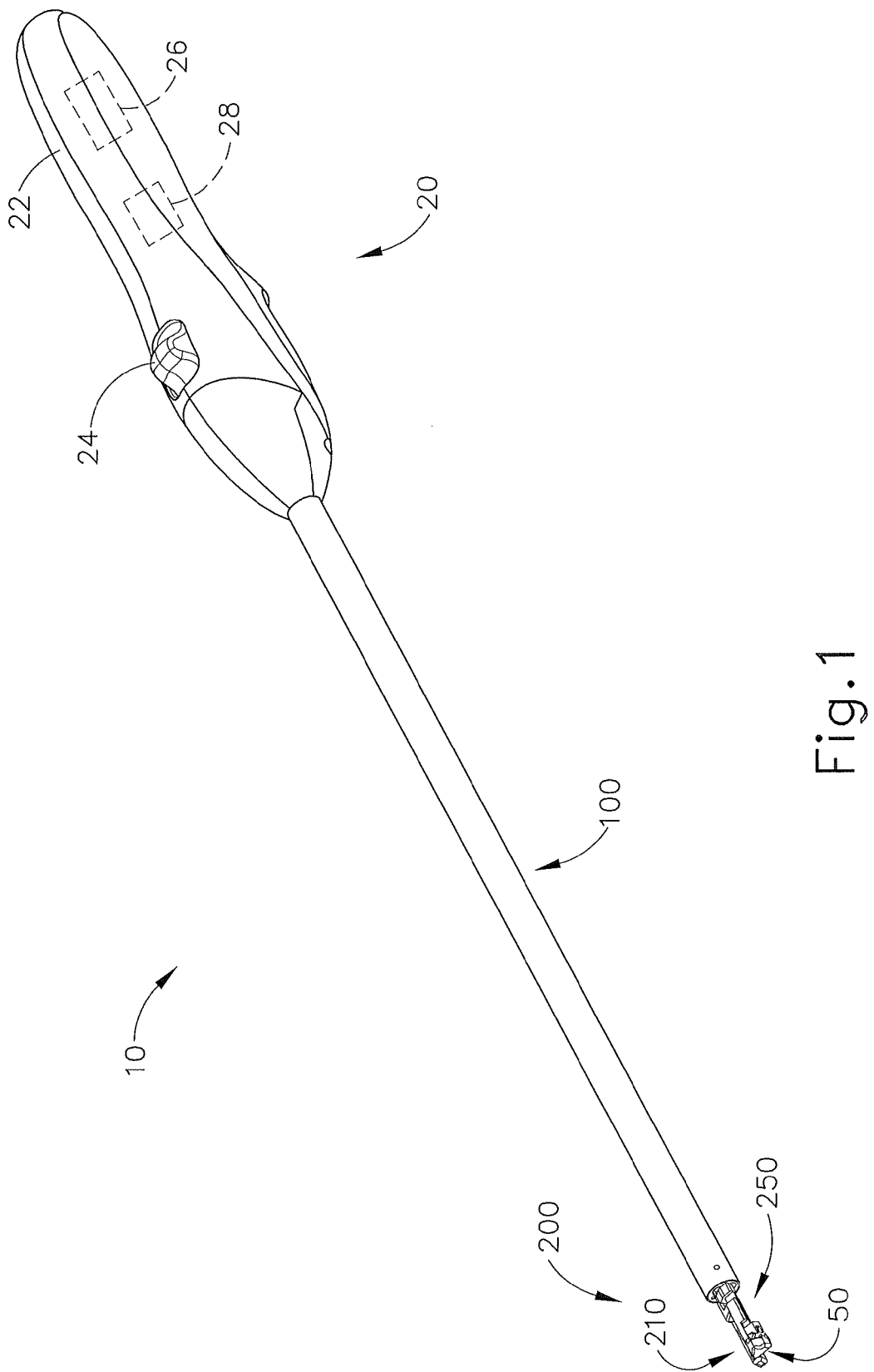
FIG. 1 depicts a perspective view of an exemplary laparoscopic suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 shows an exemplary laparoscopic suturing instrument (10). Instrument (10) of this example includes a handle portion (20), a shaft (100) extending distally from handle portion (20), and an end effector (200) at the distal end of shaft (100). Handle portion (20) includes a grip (22), a rocker (24), an integral power source (26), and a motor (28) in communication with the integral power source (26). Rocker (24) is resiliently biased to a generally vertical position (e.g., generally perpendicular to grip (22)), though rocker (24) may be rocked forwardly or rearwardly. In addition or in the alternative, rocker (24) may be rocked to the left or to the right. Rocker (24) is operable to actuate features of end effector (200) as will be described in greater detail below. Of course, rocker (24) is merely one example of a user input feature, and any other suitable type of user input feature may be used.

Integral power source (26) comprises a rechargeable battery in the present example, though it should be understood that any other suitable power source may be used. By way of example only, instrument (10) may use a power source that is external to instrument (10) (e.g., coupled with instrument (10) via a cable, etc.). Similarly, while end effector (200) is powered by motor (28) in the present example, it should be understood that any other suitable source may be used, including but not limited to a manually operable mechanism. Various other suitable components, features, and configurations for handle portion (20) will be apparent to those of ordinary skill in the art in view of the teachings herein. By way of example only, handle portion (20) may be constructed in accordance with at least some of the teachings of U.S. Provisional Patent Application No. 61/355,832, the disclosure of which is incorporated by reference herein; and/or in accordance with at least some of the teachings of U.S. patent application Ser. No. 13/156,420, now U.S. Pat. No. 9,168,037, the disclosure of which is incorporated by reference herein.

Shaft (100) of the present example has an outer diameter sized to permit shaft (100) to be inserted through a conventional trocar (not shown). Shaft (100) also has a length sized to permit end effector (200) to be positioned at a surgical site within a patient while also allowing handle portion (20) to be manipulated by a user (e.g., a surgeon) from a location outside the patient when shaft (100) is disposed in a trocar. Of course, shaft (100) need not necessarily be dimensioned for use through a trocar. For instance, instrument (10) may be used and/or configured for use in open surgical procedures.

In some versions, shaft (100) includes one or more articulating features, allowing end effector (200) to be articulated to various angles and positions relative to the longitudinal axis defined by shaft (100). Merely illustrative examples of such articulation are taught in U.S. Provisional Application Ser. No. 61/355,832, the disclosure of which is incorporated by reference herein. Various other suitable ways in which articulation may be provided will be apparent to those of ordinary skill in the art in view of the teachings herein. In addition or in the alternative, shaft (100) may be rotatable about the longitudinal axis, relative to handle portion (20), to selectively position end effector (200) at various angular orientations about the longitudinal axis. Of course, a user may rotate the entire instrument (10) about the longitudinal axis to selectively position end effector (200) at various angular orientations about the longitudinal axis.

End effector (200) of the present example includes a first grasping arm (210) and a second grasping arm (250). As will be described in greater detail below, arms (210, 250) are configured to alternatingly throw and catch a curved suturing needle (50) along a path/plane that is substantially perpendicular to the longitudinal axis defined by shaft (100). Alternatively, arms (210, 250) may be configured to alternatingly throw and catch needle (50) along a path that is substantially parallel to the longitudinal axis defined by shaft (100); or along some other path.

In some versions, arms (210, 250) pass needle (50) back and forth from arm (250) to arm (210) and from arm (250) to arm (210) in an oscillating motion (i.e., back and forth in opposite directions), such that needle (50) does not traverse a circular path as needle (50) is being passed between arms (210, 250). Such action of needle (50) may be referred to as a "reverse reset." In some other versions, needle (50) may be passed between arms (210, 250) along a circular path in a single direction. Such action of needle (50) may be referred to as a "forward reset." By way of example only, arms (210, 250) may move in accordance with at least some of the teachings of U.S. Provisional Patent Application No. 61/355,832, the disclosure of which is incorporated by reference herein; and/or in accordance with at least some of the teachings of U.S. patent application Ser. No. 13/156,420, now U.S. Pat. No. 9,168,037, the disclosure of which is incorporated by reference herein. Regardless of whether arms (210, 250) move synchronously or asynchronously, arms (210, 250) may be configured to grip and/or compress tissue that is positioned between arms (210, 250) when arms are in approximated positions, which may facilitate passage of needle (50) through the tissue.

Figure 2:
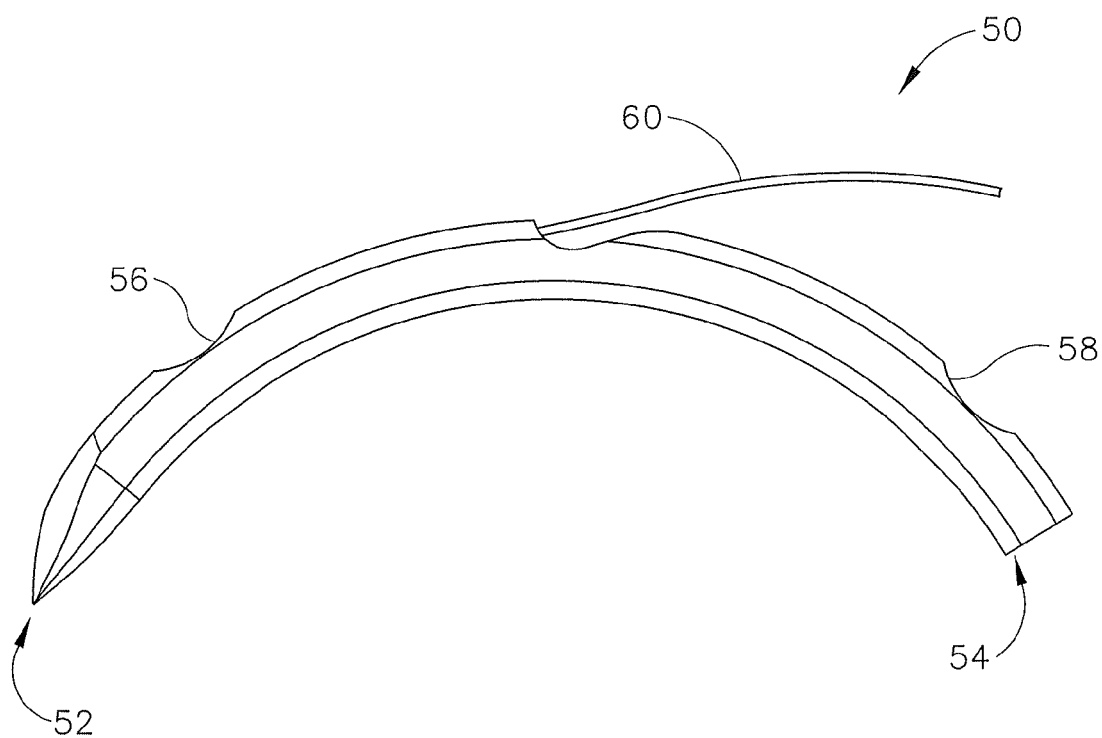
FIG. 2 depicts a side elevational view of an exemplary laparoscopic suturing needle for use with the suturing instrument of FIG. 1.
Figure 3:
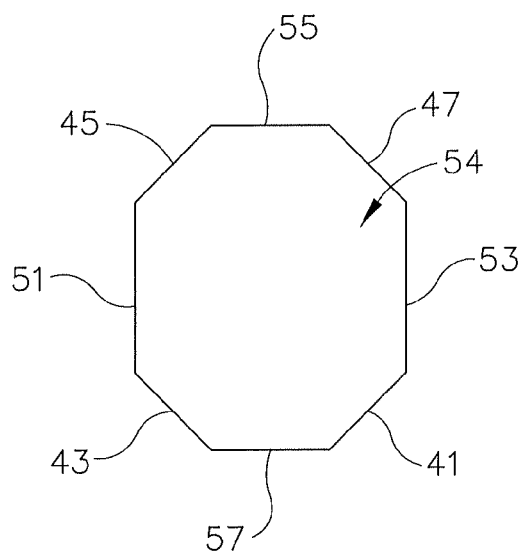
FIG. 3 depicts an end view of the blunt end of the needle of FIG. 2.

FIG. 2 shows needle (50) in greater detail. Needle (50) of this example includes a sharp tip (52), a blunt end (54), and a pair of grasping regions (56, 58) configured for grasping by arms (210, 250). In particular, grasping regions (56, 58) comprise scallops in the present example, though it should be understood that grasping regions (56, 58) may have various other configurations. FIG. 3 shows blunt end (54) of needle (50). Needle (50) has flat sides (51, 53), a top edge (55), and a bottom edge (57). Needle (50) additionally has angled sides (41, 43, 45, 47) adjacent to flat sides (51, 53), top edge (55), and bottom edge (57). Flat sides (51, 53), top edge (55), bottom edge (57), and angled sides (41, 43, 45, 47) correspond to the configuration of arms (210, 250). This will be discussed in more detail below.

Figure 2A:
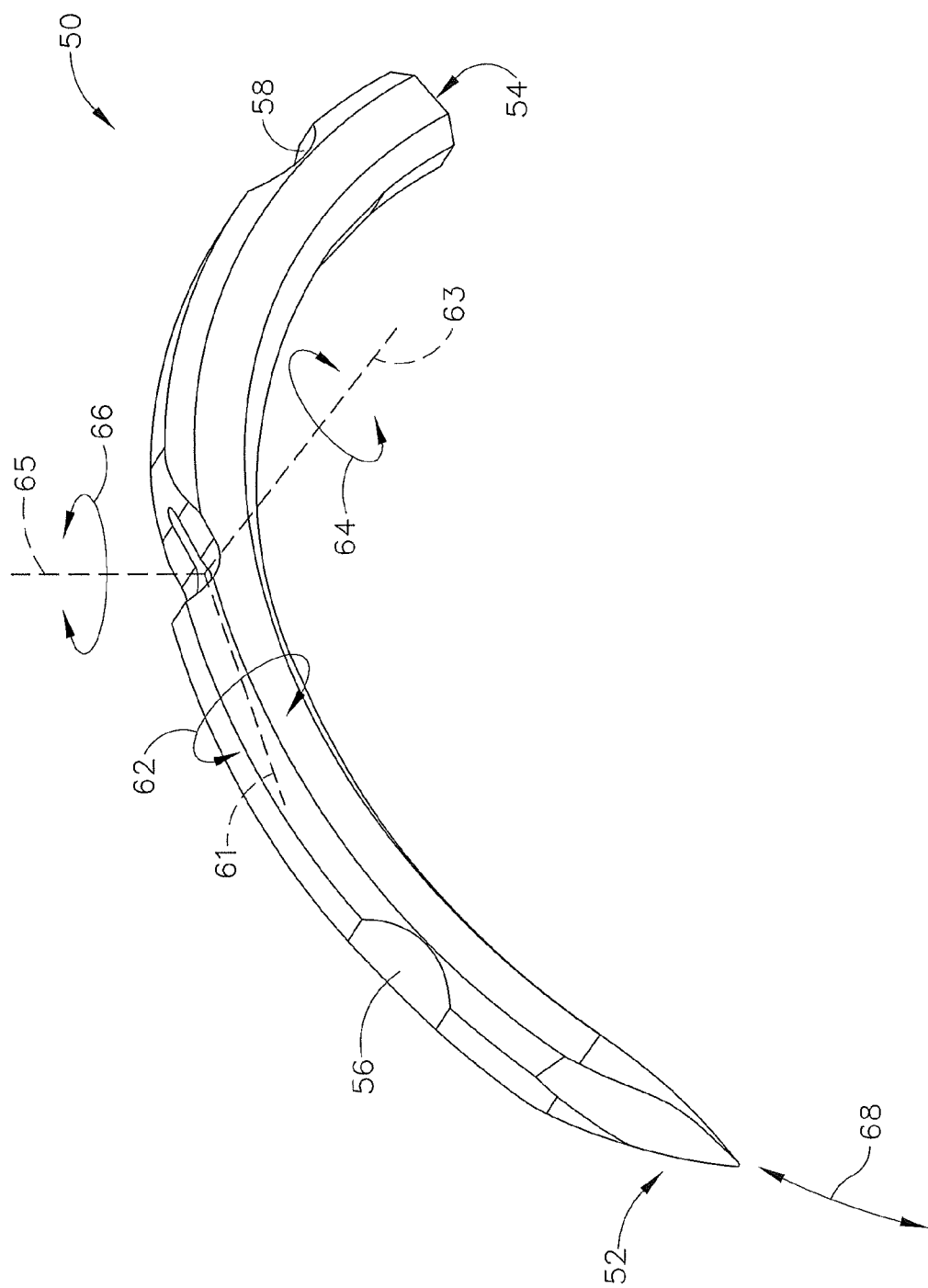
FIG. 2A depicts a perspective view of the needle of FIG. 2 showing axes of motion.

During operation of suturing instrument (10), needle (50) may become rotationally and/or translationally misaligned from arc path (68) as needle (50) is passed through tissue and between arms (210, 250). As will be described in greater detail below with reference to FIGS. 22A-22H, arc path (68) is defined as an angular path about axis (140), such that arc path (68) lies in a plane that is substantially perpendicular and transverse to shaft (100). FIG. 2A depicts three orthogonal axes (61, 63, 65) about which needle (50) may become misaligned to deviate from arc path (68) as needle (50) travels forwards and backwards between arms (210, 250). For instance, needle (50) may roll by rotating in a clockwise or counterclockwise direction about axis (61) in the direction indicated by arrow (62). Needle (50) may pitch by rotating or flexing about axis (63) in the direction indicated by arrow (64). It should be understood that axis (63) is parallel to axis (140) yet offset from axis (140) in this example. Needle (50) may yaw by rotating or flexing about axis (65) in the direction indicated by arrow (66). Of course, needle (50) may deviate from arc path (68) in various combinations of deviations about axes (61, 63, 65). As discussed in more detail below, the configurations of arms (210, 250) grasp needle (50) in a manner to realign needle (50) with arc path (68) in the event that needle (50) deviates about one or more axes (62, 64, 66). Similarly, even if needle (50) is properly aligned with arc path (68) about axes (62, 64, 66), there may be instances where needle (50) is either beyond a centered hand-off position along arc path (68) (e.g., center of grasping region (56) us past location between grasping portions (264, 274) of jaws (260, 270) or center of grasping region (58) is past location between grasping portions (224, 234) of jaws (220, 230)) or short of a centered hand-off position along arc path (68) when needle (50) is being passed from one arm (210, 250) to the other arm (210, 250). In some such instances, each arms (210, 250) is configured to properly position needle at the appropriate location along arc path (68) as control of needle (50) is being passed from one arm (210, 250) to the other arm (210, 250).

A suture (60) is secured to a mid-region of needle (50). The configuration and relationship of suture (60) and needle (50) provides an exit of suture (60) from needle (50) at an angle that is generally tangent to or oblique relative to the curvature of needle (50). Such an angle may provide reduced drag forces and/or reduced tissue trauma as compared to drag forces and/or tissue trauma that might otherwise be encountered using a needle with a suture that exits at a generally perpendicular angle.

While the example described below includes just a single strand of suture extending from the needle, it should be understood that two or more strands may extend from the needle (e.g., double leg suture, etc.). As yet another merely illustrative example, suture (60) may be secured to blunt end (54) of needle (50) instead of being secured to a mid-region of needle (50). In still other versions, end (54) includes a sharp tip instead of being blunt. It should also be understood that needle (50) may be straight instead of curved in some versions. By way of example only, needle (50) may be constructed in accordance with at least some of the teachings of U.S. Provisional Application Ser. No. 61/413,680; U.S. patent application Ser. No. 13/295,186, now U.S. Pat. No. 9,125,646; U.S. Pat. No. 6,056,771; and/or U.S. Pub. No. 2010/0100125. Still other suitable configurations for needle (50) will be apparent to those of ordinary skill in the art in view of the teachings herein.

It should also be understood that needle (50) may be constructed using various techniques. By way of example only, needle (50) may be constructed using metal-injection-molding (MIM) processes. Needle (50) may also be formed from a sheet, wire, tube, extrusion, or other components that are bent, stamped, coined, milled, otherwise machined, and/or otherwise formed. Other suitable ways in which needle (50) may be constructed will be apparent to those of ordinary skill in the art in view of the teachings herein.

II. Exemplary End Effector

As noted above, end effector (200) comprises a pair of grasping arms (210, 250) that are operable to selectively grasp needle (50) during a suturing procedure. Grasping arms (210, 250) are exposed relative to an endcap (102) of shaft (100). Each grasping arm (210, 250) extends along a respective axis that is parallel to yet offset from the center axis of shaft (100). First grasping arm (210) maintains a fixed rotational position relative to shaft (100) during operation of instrument (10) in the present example. In some other versions, first grasping arm (210) is rotatable about its own longitudinal axis, relative to shaft (100). Second grasping arm (250) of the present example is rotatable about its longitudinal axis. Such motion can be seen in the series shown by FIGS. 4A-4C.

Figure 4A:
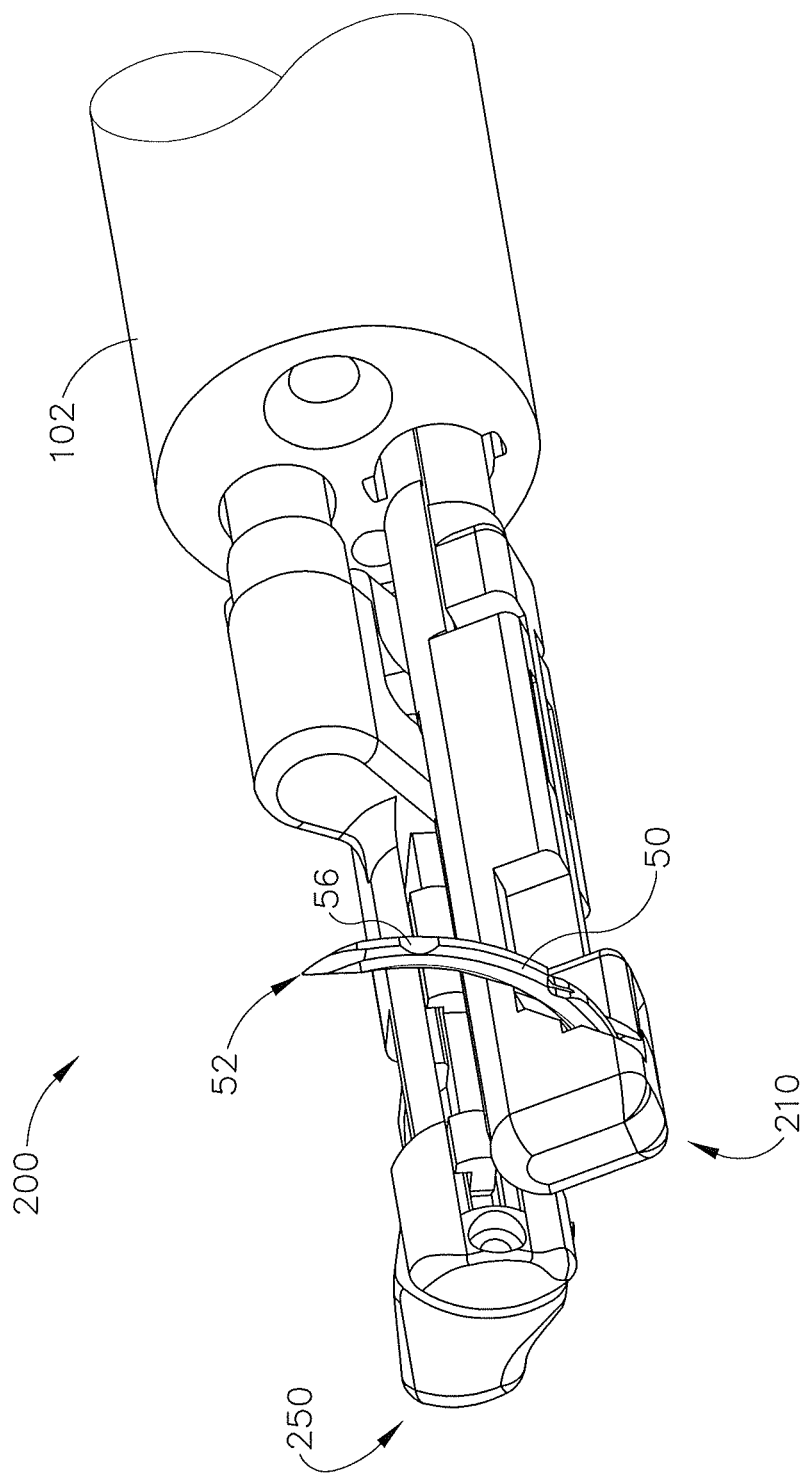
FIG. 4A depicts a perspective view of the end effector of the suturing instrument of FIG. 1 with the needle of FIG. 2, in a first operational configuration.
Figure 4B:
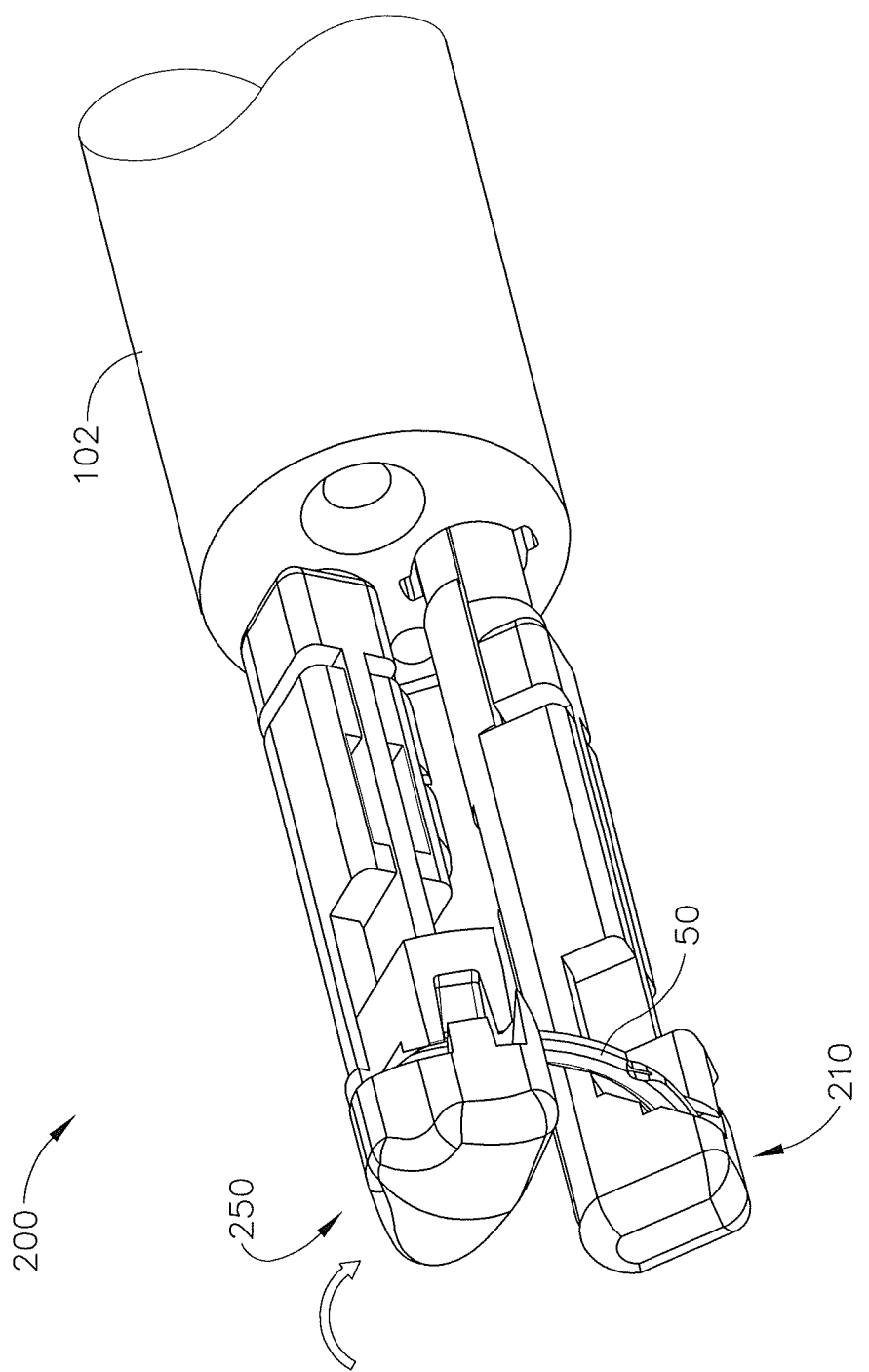
FIG. 4B depicts a perspective view of the end effector and needle of FIG. 4A, in a second operational configuration.
Figure 4C:
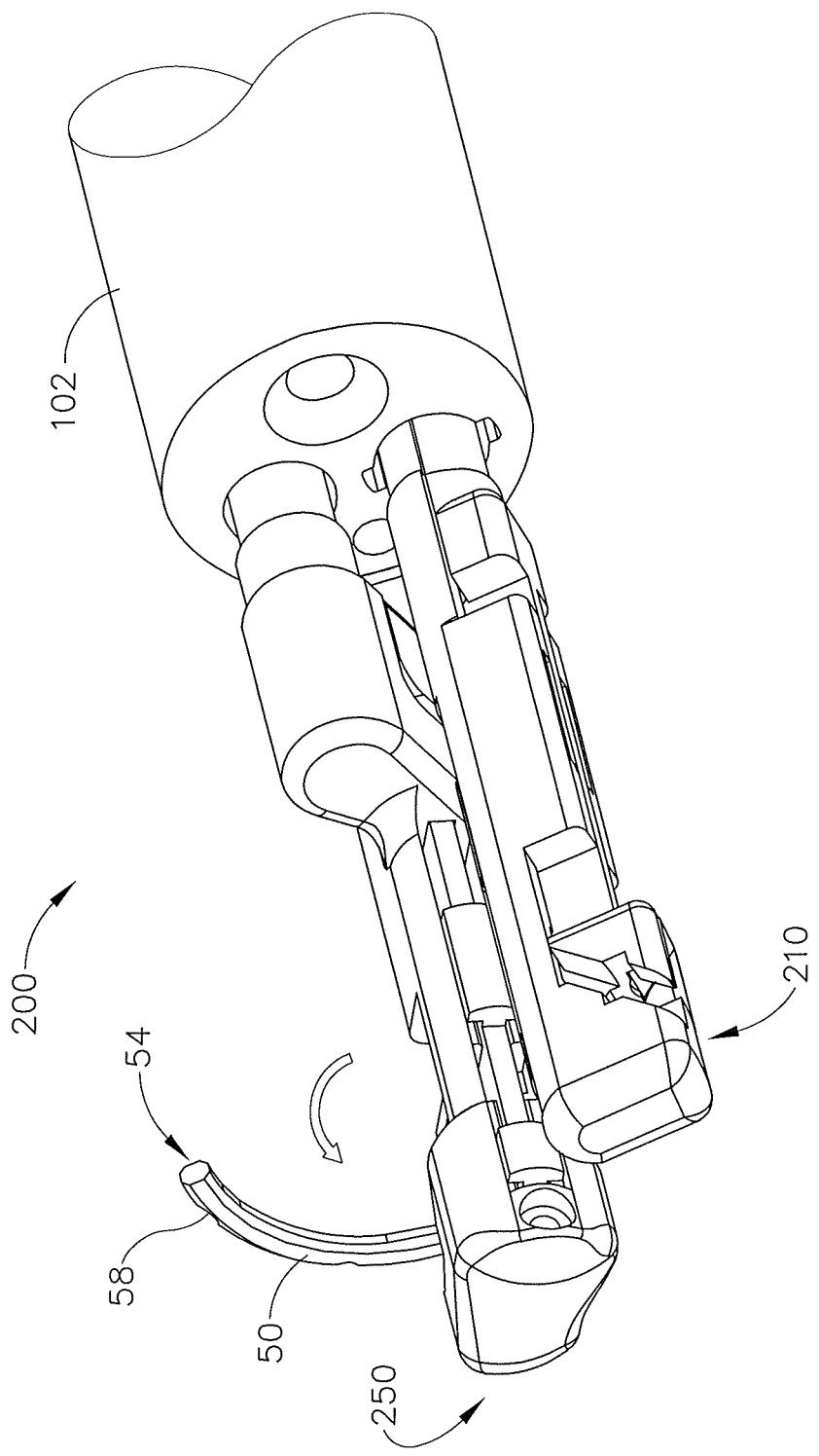
FIG. 4C depicts a perspective view of the end effector and needle of FIG. 4A, in a third operational configuration.
Figure 5:
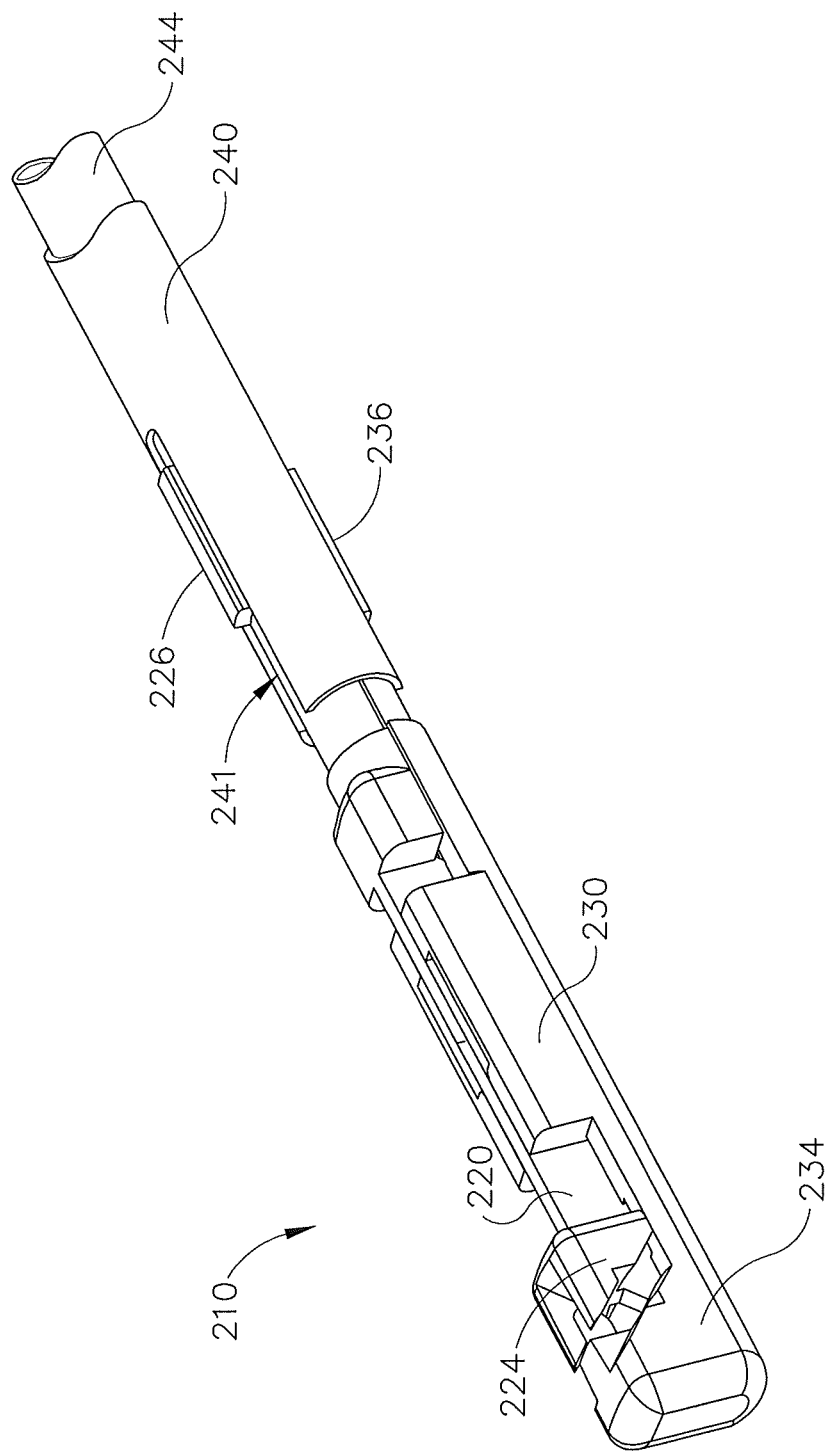
FIG. 5 depicts a first partial perspective view of a first needle grasping arm of the end effector of FIG. 4A.
Figure 6:
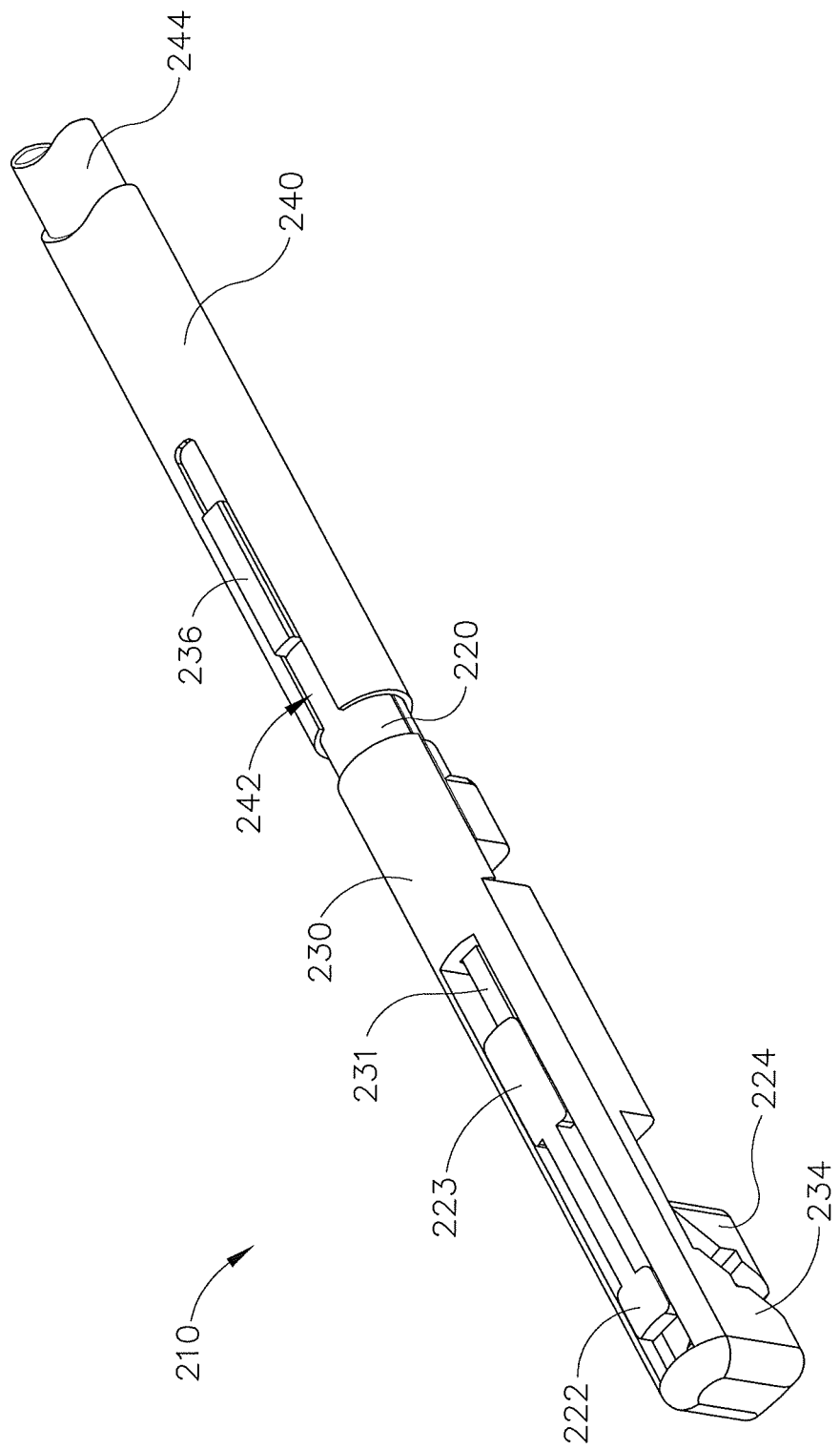
FIG. 6 depicts a second partial perspective view of the first needle grasping arm of FIG. 5.

FIG. 4A shows first grasping arm (210) grasping needle (50), with second grasping arm (250) rotated away from needle (50), exposing sharp tip (52) of needle (50). FIG. 4B shows second grasping arm (250) rotated toward needle (50) to a position enabling second grasping arm (250) to grasp needle (50) and first grasping arm (210) to release needle (50). FIG. 4C shows second grasping arm (250) rotated away from first grasping arm (210), pulling needle (50) away from second grasping arm (250). After reaching this position, second grasping arm (250) may be rotated back to the position shown in FIG. 4B, to thereby pass needle (50) back to first grasping arm (210); then rotate back to the position shown in FIG. 4A to start the cycle over again.

In the examples described herein, needle (50) is driven along a plane that is substantially perpendicular to the longitudinal axis of shaft (100). In some other examples, needle (50) is driven along a plane that is oblique relative to the longitudinal axis of shaft (100) or substantially parallel to the longitudinal axis of shaft (100). During some uses of instrument (10), needle (50) may deviate from the desired perpendicular plane. Such deviation may be due to manufacturing tolerances, deflections caused by tissue or other structures, and/or for other reasons. Such deviation may be accentuated by using a needle (50) having a relatively great length. As will be described below, end effector (200) of the present example is configured to readily accommodate and correct such off-plane deviations. In other words, arms (210, 250) are operable to grasp needle (50) even in instances where needle (50) has deviated away from the expected perpendicular plane of motion; and arms (210, 250) are further operable to redirect a deviated needle (50) back onto the expected perpendicular plane of motion.

It should be noted that suture (60) is omitted from FIGS. 4A-4C for clarity. Various components of grasping arms (210, 250) will be described in greater detail below. Various ways in which grasping arms (210, 250) may be used will also be described in greater detail below. Other suitable components of and uses for grasping arms (210, 250) will be apparent to those of ordinary skill in the art in view of the teachings herein.

A. Exemplary First Grasping Arm

FIGS. 5-12 show first grasping arm (210) in greater detail. First grasping arm (210) comprises a first jaw (220) and a second jaw (230). Jaws (220, 230) are substantially aligned with each other and are slidable longitudinally relative to each other. Jaw (220) includes a pair of flanges (222, 223) that are received through corresponding openings (232, 233) of jaw (230) during assembly of arm (210). Thereafter, flanges (222, 223) prevent jaws (220, 230) from deflecting transversely away from each other. Jaws (220, 230) also include complementary needle grasping features (224, 234) that are configured to selectively grasp needle (50) as will be described in greater detail below. The proximal portion of jaw (220) includes a transversely extending fin (226). Likewise, the proximal portion of jaw (230) also includes a transversely extending fin (236). Fins (226, 236) are slidably disposed in corresponding distal slots (241, 242) of a sheath (240). Sheath (240) extends along the length of shaft (100) and is substantially fixed within shaft (100). In particular, sheath (240) does not rotate or translate relative to shaft (100) in this example. Sheath (240) thus provides a mechanical ground in the angular direction. It should therefore be understood that the relationship between fins (226, 236) and slots (241, 242) prevent first grasping arm (210) from rotating relative to shaft (100). In some other versions, however, first grasping arm (210) is roatatable relative to shaft (100) (e.g., by rotating sheath (240) within shaft (100), etc.). It should also be understood that, in the present example, the relationship between fins (226, 236) and slots (241, 242) still permits jaws (220, 230) to translate relative to sheath (240) and shaft (100).

Figure 7A:
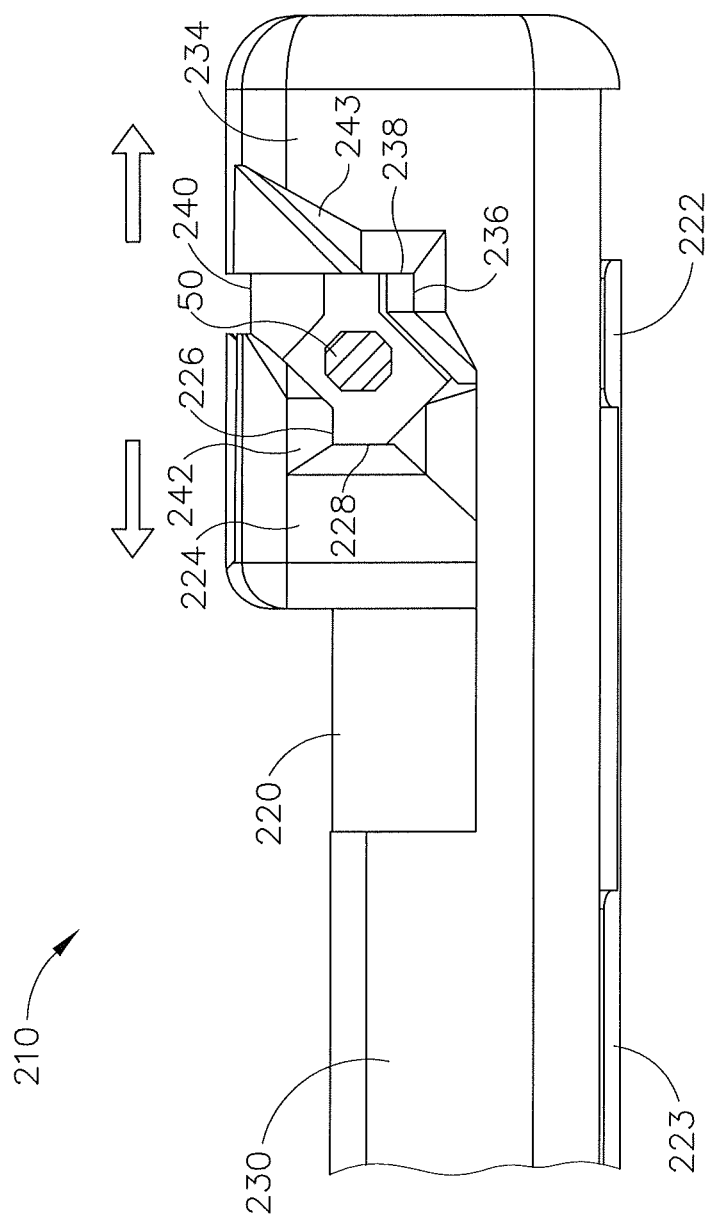
FIG. 7A depicts a partial side elevational view of the first needle grasping arm of FIG. 5, in a first operational configuration.
Figure 7B:
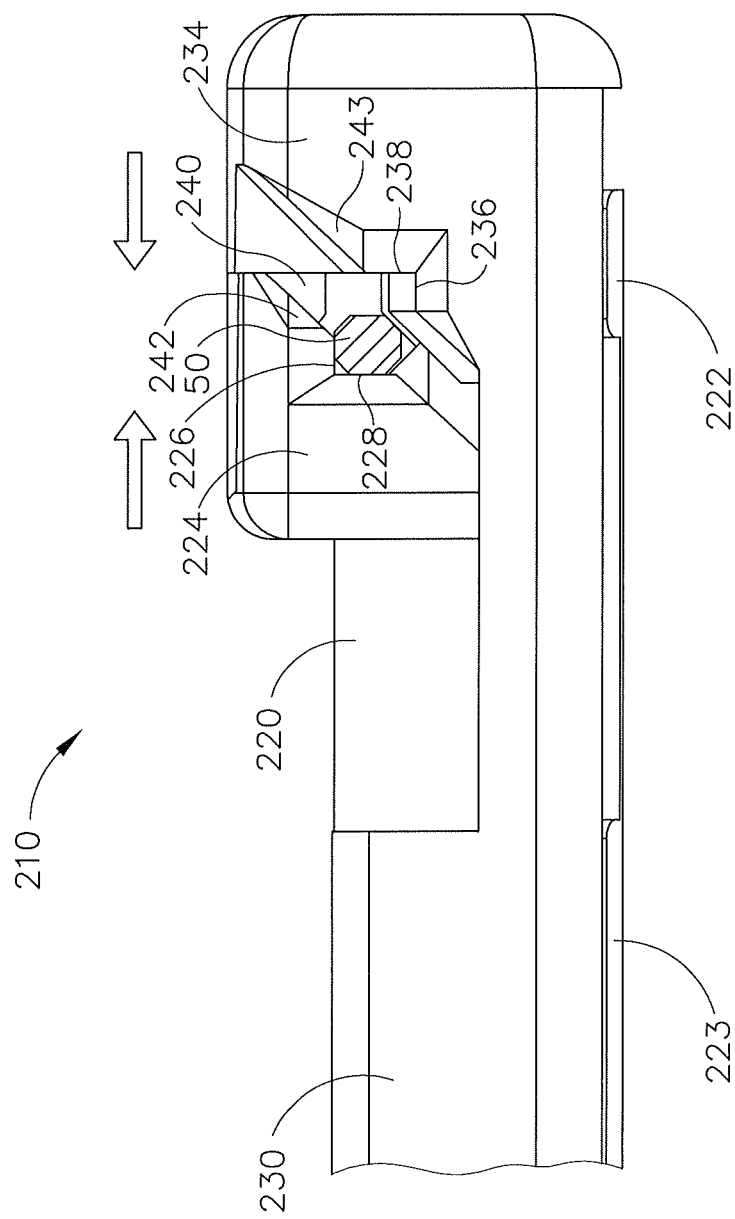
FIG. 7B depicts a partial side elevational view of the first needle grasping arm of FIG. 5, in a second operational configuration.

As best seen in FIGS. 7A-7B, jaws (220, 230) are simultaneously movable in opposite directions to selectively expand or reduce an opening formed by grasping features (224, 234) to receive needle (50). For instance, in FIG. 7A, jaw (220) has moved proximally toward shaft (100) and jaw (230) has simultaneously moved distally away from shaft (100) to enlarge the opening defined by grasping features (224, 234) to receive needle (50). In FIG. 7B, jaw (220) has moved distally away from shaft (100) and jaw (230) has simultaneously moved proximally toward shaft (100) to reduce the opening defined by grasping features (224, 234) to securely grasp needle (50). In some other versions, one jaw (220, 230) remains longitudinally stationary while the other jaw translates longitudinally to grasp or release needle (50) between grasping features (224, 234). However, it should be understood that in versions such as the present example where jaws (220, 230) both move simultaneously in opposite directions, such motion may further promote alignment of needle (50) within grasping features (224, 234) as compared to versions where one jaw (220, 230) always stays longitudinally fixed relative to shaft (100). In other words, having both grasping features (224, 234) always spaced equidistantly away from the intended path of needle (50) (regardless of whether jaws (220, 230) are open as shown in FIG. 7A or closed as shown in FIG. 7B) may better accommodate incidental deflections of needle (50) away from that intended path in either direction during use of instrument (10). Arm (210) may thus be particularly suited to accommodate instances where needle (50) has deviated away from the expected perpendicular plane of motion as described above.

Figure 8:
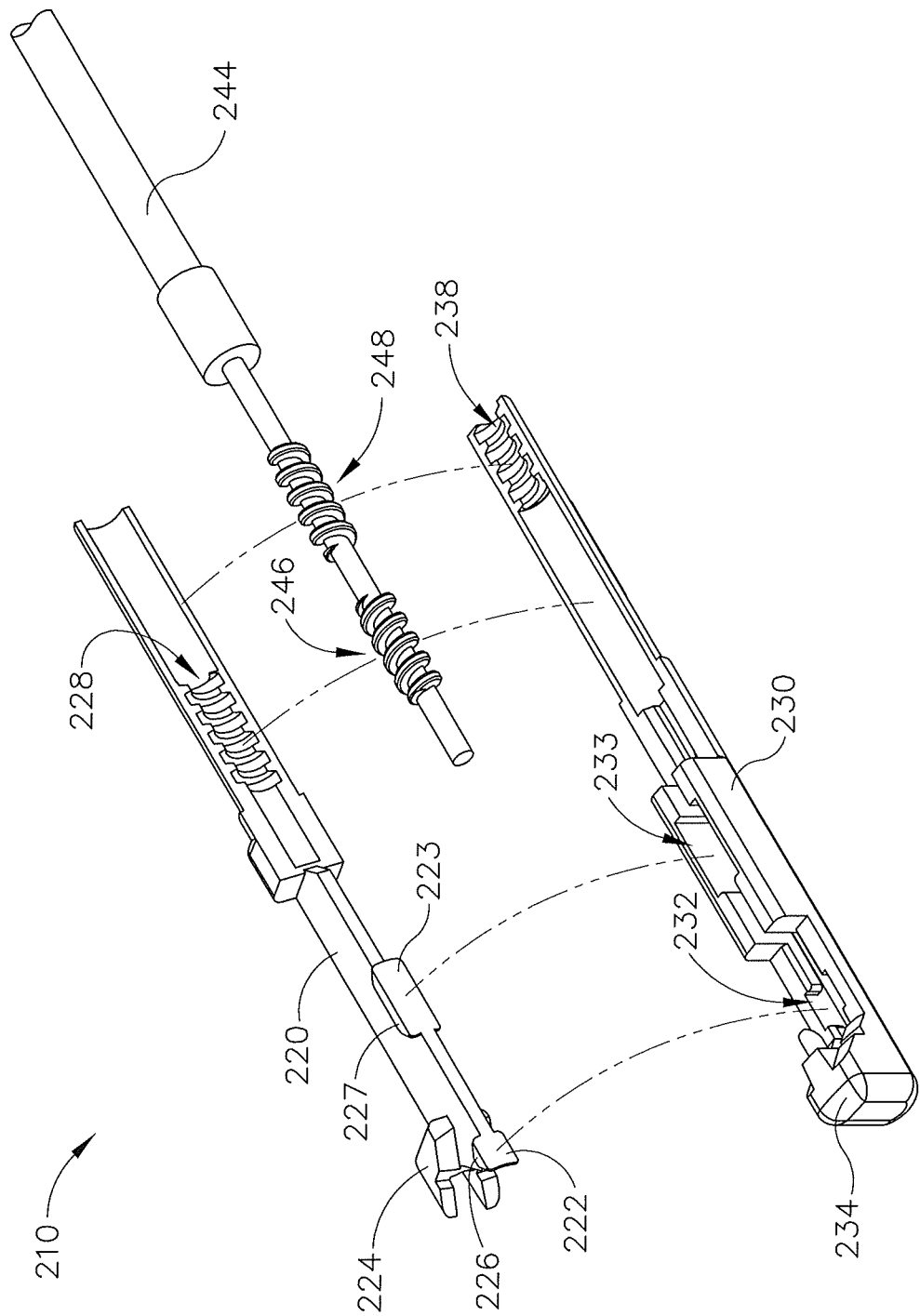
FIG. 8 depicts a partial exploded view of the first needle grasping arm of FIG. 5.

FIG. 8 shows exemplary features that may be used to provide the simultaneous opposing motion of jaws (220, 230) described above. In particular, FIG. 8 shows a drive shaft (244) that includes a first threaded section (246) and a second threaded section (248). Drive shaft (244) is coaxially positioned within sheath (240) and is rotatable within sheath (240). Drive shaft (244) is rotatably driven by motor (28) in handle portion (20). The threading of first threaded section (246) is oriented opposite to the threading of second threaded section (248), such that threaded sections (246, 248) have opposite pitches. The proximal portions of jaws (220, 230) together encompass the distal portion of drive shaft (244). In particular, the proximal portion of jaw (220)

includes threading (228) that meshes with first threaded section (246); while the proximal portion of jaw (230) includes threading (238) that meshes with second threaded section (248). It should therefore be understood that threading (228) has a pitch that is opposite to the pitch of threading (238). It should also be understood that, due to the relationships and orientations of threaded sections (246, 248) and threading (228, 238), drive shaft (244) will cause jaws (220, 230) to simultaneously translate away from each other (FIG. 7A) when drive shaft (244) is rotated in one direction; while drive shaft (244) will cause jaws (220, 230) to simultaneously translate toward each other (FIG. 7B) when drive shaft (244) is rotated in the other direction.

It should be understood that the opposing thread configuration described above may require relatively low torsional force to rotate drive shaft (244) to drive jaws (220, 230) toward and away from each other. It should also be understood that the opposing thread configuration described above may provide a relatively high holding force. For instance, when needle grasping features (224, 234) are driven toward each other to secure needle (50) as shown in FIG. 7B, and needle (50) is off-plane for whatever reason (e.g., incidentally oriented slightly obliquely relative to the longitudinal axis of shaft (100), etc.), the needle holding forces at grasping features (224, 234) may be self-reinforcing due to opposing forces provided through the opposing thread configuration described above, providing a mechanical advantage to urge needle (50) back into the desired planar orientation, even if tissue or some other structure is resisting such movement of needle into the desired planar orientation. Similarly, the opposing thread configuration described above may provide friction that acts as an anti-backup feature, substantially resisting inadvertent separation of grasping features (224, 234), thereby providing a very secure hold of needle (50).

Flanges (222, 223) may also include ramped interfaces with slot (231) to reduce the likelihood of jaws (220, 230) longitudinally separating while in the closed position shown in FIG. 7B. In FIG. 8, flange (222) has a ramped portion (226) extending outward along the perimeter edges of flange (222). Flange (223) is also configured with a ramped portion (227) extending outward along the perimeter edges of flange (223). Slot (231) on jaw (230) has a ramped portion extending inwardly along its sidewalls to correspond to the ramped portion (226, 227) of flanges (222, 233). Flanges (222, 223) and slot (231) may extend in another direction as will be apparent to one with ordinary skill in the art in view of the teachings herein. Ramped portions (226, 227) of flanges (222, 223) and slot (231) may interface to provide an additional interlocking interface between jaws (220, 230). Accordingly, when jaws (220, 230) are in a closed position to grasp needle (50), ramped portions (226, 277) provide additional forces to impinge against top edge (55) and bottom edge (57) of needle (50). Ramped portions (226, 227) may also include an elastic material to increase the friction between jaws (220, 230). Other suitable components that may be used to provide opposing motion of grasping features (224, 234) (e.g., a pinion with opposing racks, etc.) will be apparent to those of ordinary skill in the art in view of the teachings herein.

As noted above, drive shaft (244) may be selectively driven in either rotational direction by motor (28), such as in response to actuation of rocker (24). Alternatively, any other motive source and/or user input feature may be used. It should also be understood that, while drive shaft (244) rotates about an axis that is parallel to the axis of shaft (100), alternative drive systems that include a rotary member may provide rotation of such a rotary member about an axis that is not parallel to the axis of shaft (100). For instance, a pinion based drive system may provide rotation of a drive pinion about an axis that is perpendicular to the axis of shaft (100). Other suitable ways in which jaws (220, 230) may be actuated will be apparent to those of ordinary skill in the art in view of the teachings herein.

1. Exemplary First Grasping Feature

Figure 9:
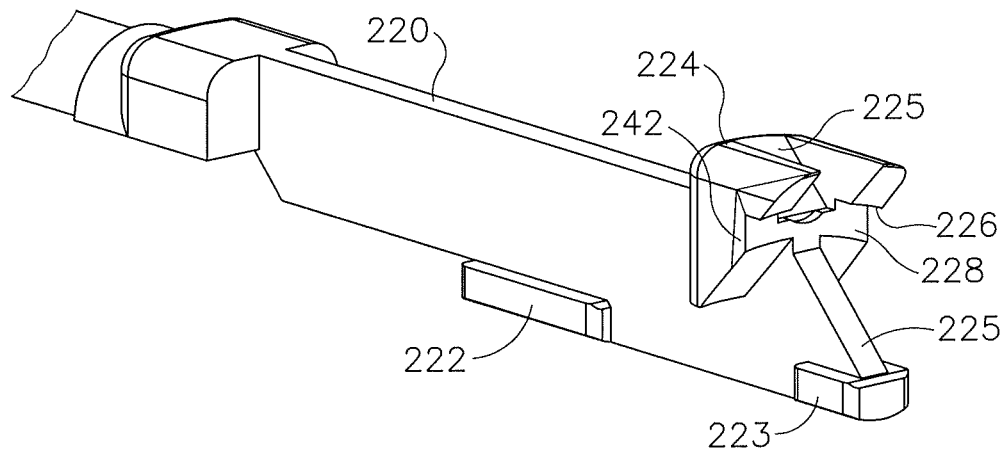
FIG. 9 depicts a partial perspective view of a first needle grasping feature of the first needle grasping arm of FIG. 5.
Figure 10:
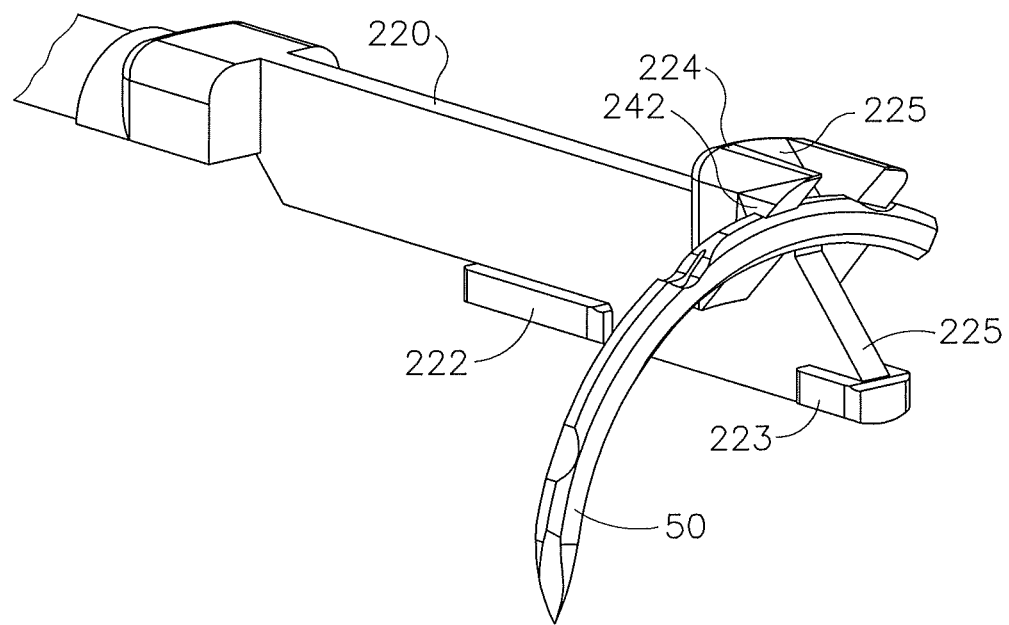
FIG. 10 depicts a partial perspective view of the first needle grasping feature of FIG. 9 engaged with the needle of FIG. 2.

FIGS. 9 and 10 show a more detailed view of first grasping feature (224) of first jaw (220). First grasping feature (224) includes chamfered lead-in surfaces (242), mating interfaces (226, 228), and ramp (225). First grasping feature (224) has chamfered lead-in surfaces (242) on the side surfaces to guide needle (50) into first grasping feature (224). Mating interface (226) extends horizontally from first grasping feature (224) to align with top edge (55) of needle (50). Mating interface (228) extends vertically from first grasping feature (224) to align with side edge (53) of needle (50). Ramp (225) interfaces with second grasping feature (234) to provide a more secure grip on needle (50). This is discussed in greater detail below.

If needle (50) is misaligned from arc path (68) about one or more axes (61, 63, 65) as needle (50) is passed from second grasping arm (250) to first grasping arm (210), chamfered lead-in surfaces (242), mating surfaces (226, 228), and ramp (225) work to realign and guide needle (50) into an aligned position in first grasping arm (210) as grasping features (224, 234) translate toward each other. For instance, if needle (50) is rolled about axis (61), mating surface (226) interfaces with top edge (55) of needle (50), mating surface (228) interfaces with side edge (53) of needle (50), and ramp (225) interfaces with bottom edge (57) of needle (50) to realign needle (50) about axis (61). Angled sides (41, 47) of needle (50) are adjacent to top edge (55) and side edge (53) to help guide needle (50) to mating surfaces (226, 228) in the event that needle (50) is rolled about axis (61). If needle (50) is pitched about axis (63) or yawed about axis (65), chamfered lead-in surfaces (242) guide needle (50) into first grasping feature (224) to realign needle (50) about axes (63, 65). Mating surfaces (226, 228) then cooperate with surfaces (236, 238) of second jaw (230), as will be described in greater detail below, to hold needle (50) in the aligned arc path (68) position in first grasping feature (224).

2. Exemplary Second Grasping Feature

Figure 11:
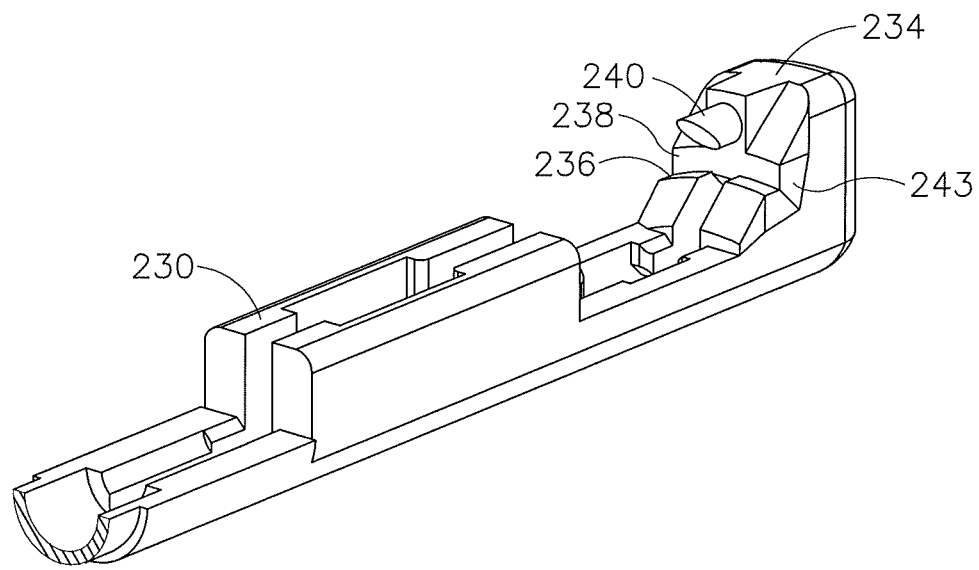
FIG. 11 depicts a partial perspective view of a second needle grasping feature of the first needle grasping arm of FIG. 5.
Figure 12:
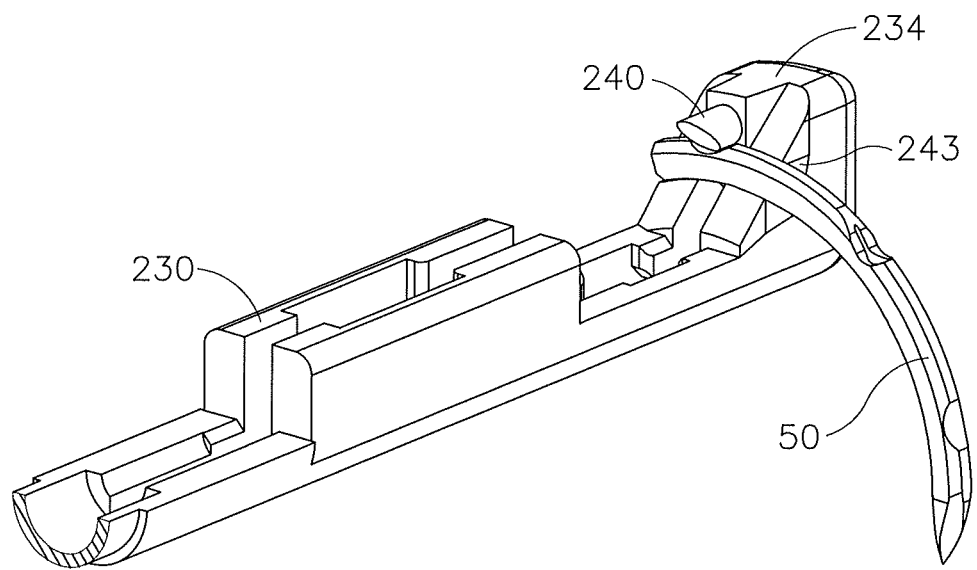
FIG. 12 depicts a partial perspective view of the second needle grasping feature of FIG. 11 engaged with the needle of FIG. 2.
Figure 13:
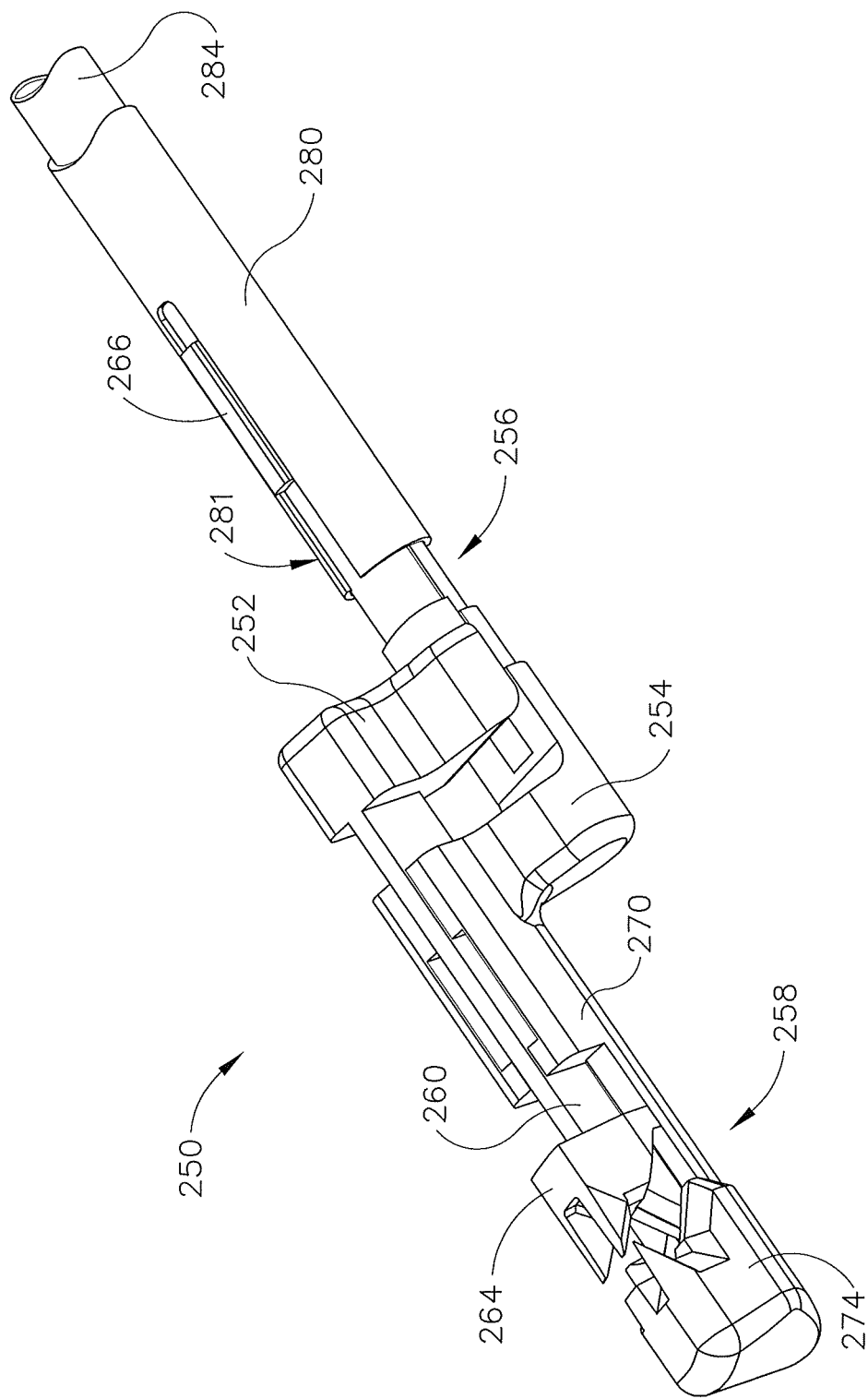
FIG. 13 depicts a first partial perspective view of a second needle grasping arm of the end effector of FIG. 4A.
Figure 14:
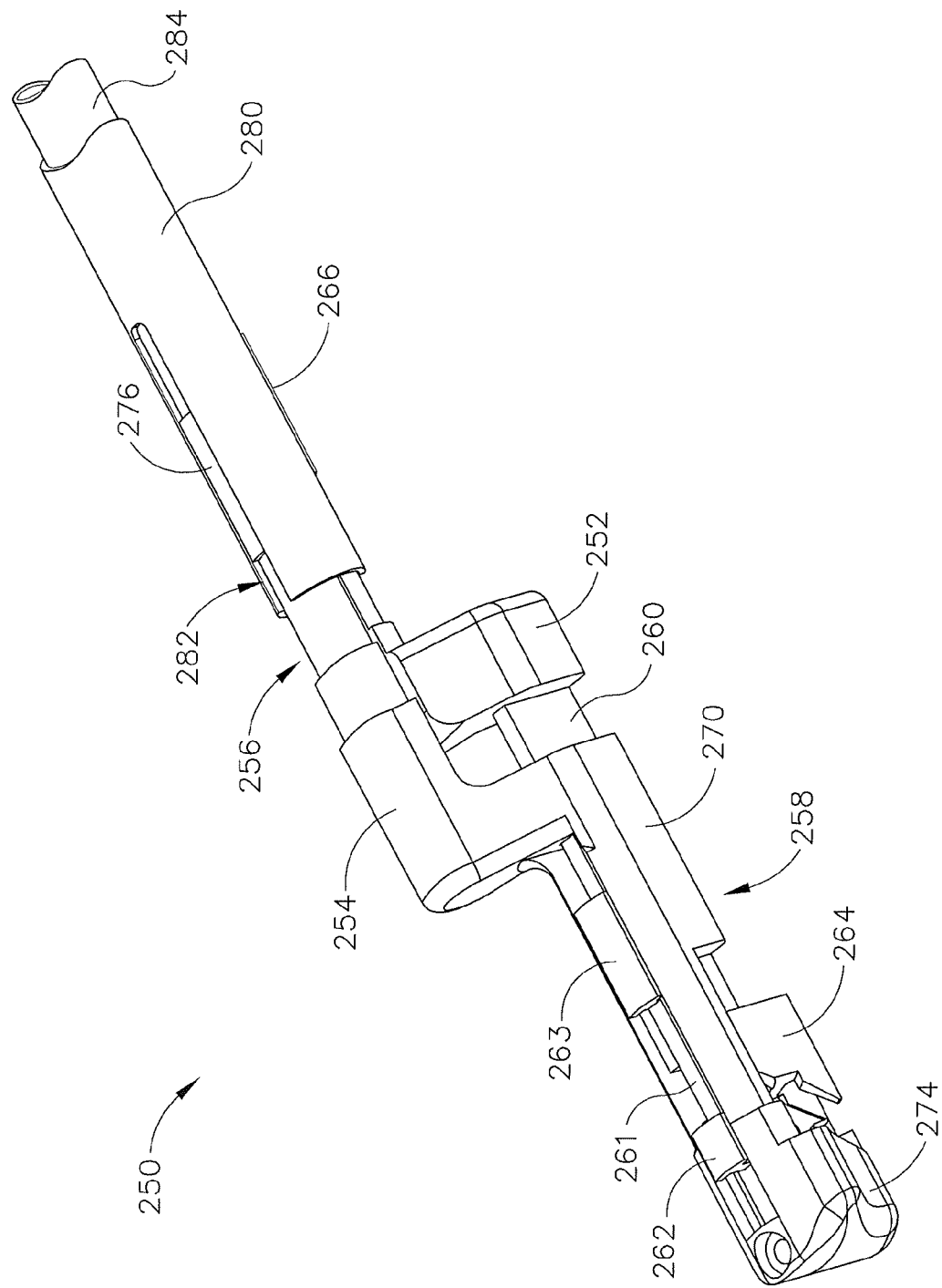
FIG. 14 depicts a second partial perspective view of the second needle grasping arm of FIG. 13.

FIGS. 11 and 12 show a more detailed view of second grasping feature (234) of second jaw (230). Second grasping feature (234) includes chamfered lead-in surfaces (243), mating interfaces (236, 238), and location feature (240). Second grasping feature (234) has chamfered lead-in surfaces (243) on the side surfaces to guide needle (50) into second grasping feature (224). Mating interface (236) extends horizontally from second grasping feature (234) to align with bottom edge (57) of needle (50). Mating interface (238) extends vertically from second grasping feature (234) to align with side edge (51) of needle (50). Locating feature (240) extends proximally from the top portion of second grasping feature (234). As shown in FIG. 11, locating feature (240) has a cylindraceous configuration to correspond to grasping region (58) of needle (50). Locating feature (240) also has a chamfered free end. Of course, location feature (240) and grasping region (58) may have any other suitable configuration as will be apparent to one with ordinary skill in the art in view of the teachings herein.

As needle (50) is passed from second grasping arm (250) to first grasping arm (210), needle (50) proceeds into first grasping arm (210) until location feature (240) is generally aligned with grasping region (58) of needle (50). If needle (50) is aligned with arc path (68) yet is improperly positioned along arc path (68), the configurations of location feature (240) and grasping region (58) cooperate to properly position needle (50) along arc path (68) as jaws (220, 230) are closed together. Ramp (225) may further cooperate with bottom edge (57) of needle (50) to assist in driving grasping region (58) into a substantially centered position adjacent to location feature (240).

If needle (50) is misaligned from arc path (68) about one or more axes (61, 63, 65) as needle (50) is passed to first grasping arm (210), chamfered lead-in surfaces (243) and mating surfaces (236, 238) work to realign and guide needle (50) into an aligned position in first grasping arm (210) as grasping features (224, 234) translate toward each other. For instance, if needle (50) is rolled about axis (61), mating surface (236) interfaces with bottom edge (57) of needle (50) and mating surface (238) interfaces with side edge (51) of needle (50) to realign needle (50) about axis (61). Angled sides (43, 45) of needle (50) are adjacent to bottom edge (57) and side edge (51) to help guide needle (50) to mating surfaces (236, 238) in the event that needle (50) is rolled about axis (61). If needle (50) is pitched about axis (63) or yawed about axis (65), chamfered lead-in surfaces (243) guide needle (50) into second grasping feature (234) to realign needle (50) about axes (64, 66). Mating surfaces (236, 238) then cooperate with surfaces (226, 228) of first jaw (220) to hold needle (50) in the aligned arc path (68) position in second grasping feature (234).

As shown in FIGS. 7A-7B, first grasping feature (224) presents a U-shaped profile (turned on its side in FIGS. 7A-7B). Mating surface (226) forms one leg of the U-shaped configuration, mating surface (228) forms the base of the U-shaped configuration, and ramp (225) forms the other leg of the U-shaped configuration. Second grasping feature (234) has a corresponding but oppositely oriented U-shaped profile. Locating feature (240) forms one leg of the U-shaped configuration, mating surface (238) forms the base of the U-shaped configuration, and mating surface (236) forms the other leg of the U-shaped configuration. The U-shaped profiles of first grasping feature (224) and second grasping feature (234) are substantially separated when first grasping arm (210) is in an open configuration as shown in FIG. 7A. The U-shaped profiles then substantially overlap when first grasping arm (210) is in a closed configuration as shown in FIG. 7B. The overlap of the U-shaped configurations may assist in providing a substantially secure grip of needle (50) by first grasping arm (210).

B. Exemplary Second Grasping Arm

FIGS. 13-21 show second grasping arm (250) in greater detail. Second grasping arm (250) comprises a first jaw (260) and a second jaw (270). Jaws (260, 270) are substantially aligned with each other and are slidable longitudinally relative to each other. Jaw (260) includes a pair of flanges (262, 263) that are received through corresponding openings (272, 273) of jaw (270) during assembly of arm (250). Thereafter, flanges (262, 263) prevent jaws (260, 270) from deflecting transversely away from each other. Jaws (260, 270) also include complementary needle grasping features (264, 274) that are configured to selectively grasp needle (50) as will be described in greater detail below. The proximal portion of jaw (260) includes a transversely extending fin (266). Likewise, the proximal portion of jaw (270) also includes a transversely extending fin (276). Fins (266, 276) are slidably disposed in corresponding distal slots (281, 282) of a sheath (280), which will be described in greater detail below. Each jaw (260, 270) of second grasping arm (250) includes a dogleg section (252, 254). Each dogleg section (252, 254) forms a pair of right angles between a proximal portion (256) of grasping arm (250) and a distal portion (258) of grasping arm (250). The configuration of dogleg sections (252, 254) provides distal portion (258) in a parallel yet offset position relative to proximal portion (256). Thus, when grasping arm (250) is rotated about a longitudinal axis extending along the length of the proximal portion (256) of grasping arm (250), the distal portion (258) of grasping arm (250) rotates in an orbital motion about that longitudinal axis. Such motion will be described in greater detail below.

Sheath (280) extends along the length of shaft (100) and is partially fixed within shaft (100). In particular, sheath (280) does not translate relative to shaft (100) in this example, though sheath (280) is rotatable relative to shaft (100). For instance, sheath (280) may be selectively rotated in either direction by motor (28) (e.g., in response to actuation of rocker (24), etc.). It should therefore be understood that rotation of sheath (280) relative to shaft (100) will provide rotation of second grasping arm (250) relative to shaft (100), due to the relationship between fins (266, 276) and slots (281, 282). As noted above, when second grasping arm (250) is rotated by sheath (280), the distal portion (258) of grasping arm (250) rotates in an orbital motion about the longitudinal axis that is defined by both sheath (280) and the proximal portion (256) of grasping arm (250). In some other versions, second grasping arm (250) is non-roatatable relative to shaft (100). It should also be understood that, in the present example, the relationship between fins (266, 276) and slots (281, 282) permits jaws (260, 270) to translate relative to sheath (280) and shaft (100).

Figure 15A:
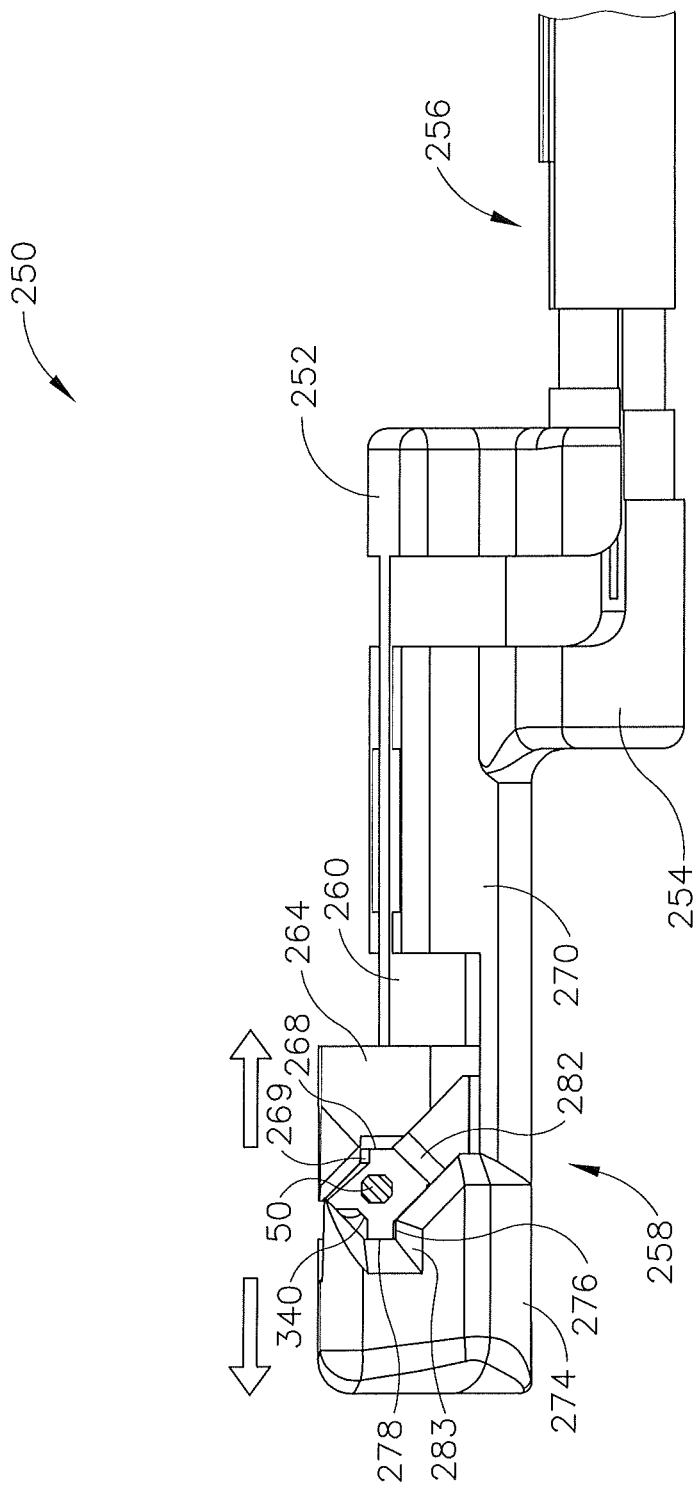
FIG. 15A depicts a partial side elevational view of the second needle grasping arm of FIG. 13, in a first operational configuration.
Figure 15B:
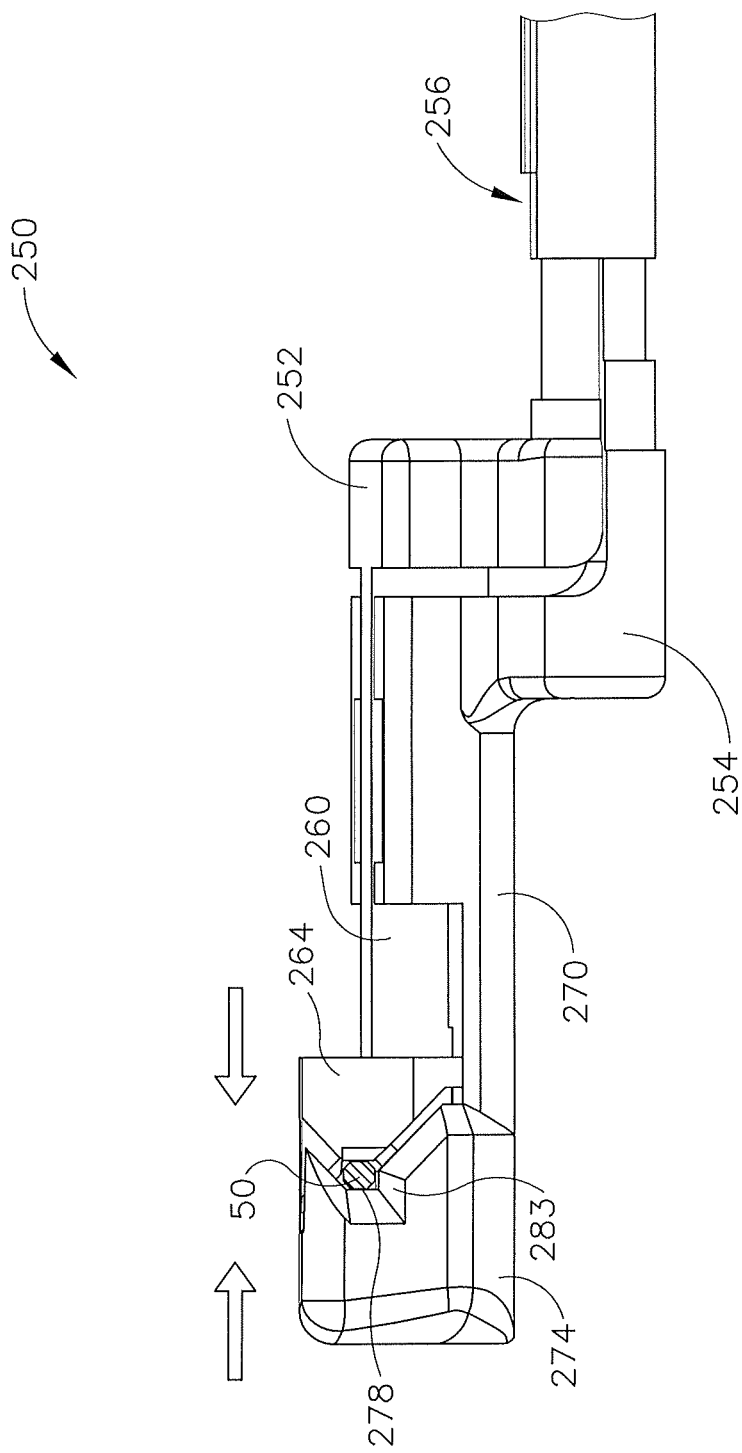
FIG. 15B depicts a partial side elevational view of the second needle grasping arm of FIG. 13, in a second operational configuration.

As best seen in FIGS. 15A-15B, jaws (260, 270) are simultaneously movable in opposite directions to selectively expand or reduce an opening formed by grasping features (264, 274) to receive needle (50). For instance, in FIG. 15A, jaw (260) has moved proximally toward shaft (100) and jaw (270) has simultaneously moved distally away from shaft (100) to enlarge the opening defined by grasping features (264, 274) to receive needle (50). In FIG. 15B, jaw (260) has moved distally away from shaft (100) and jaw (270) has simultaneously moved proximally toward shaft (100) to reduce the opening defined by grasping features (264, 274) to securely grasp needle (50). In some other versions, one jaw (260, 270) remains longitudinally stationary while the other jaw translates longitudinally to grasp or release needle (50) between grasping features (264, 274). However, it should be understood that in versions such as the present example where jaws (260, 270) both move simultaneously in opposite directions, such motion may further promote alignment of needle (50) within grasping features (264, 274) as compared to versions where one jaw (260, 270) always stays longitudinally fixed relative to shaft (100). In other words, having both grasping features (264, 274) always spaced equidistantly away from the intended path of needle (50) (regardless of whether jaws (260, 270) are open as shown in FIG. 15A or closed as shown in FIG. 15B) may better accommodate incidental deflections of needle (50) away from that intended path in either direction during use of instrument (10). Arm (250) may thus be particularly suited to accommodate instances where needle (50) has deviated away from the expected perpendicular plane of motion as described above.

Figure 16:
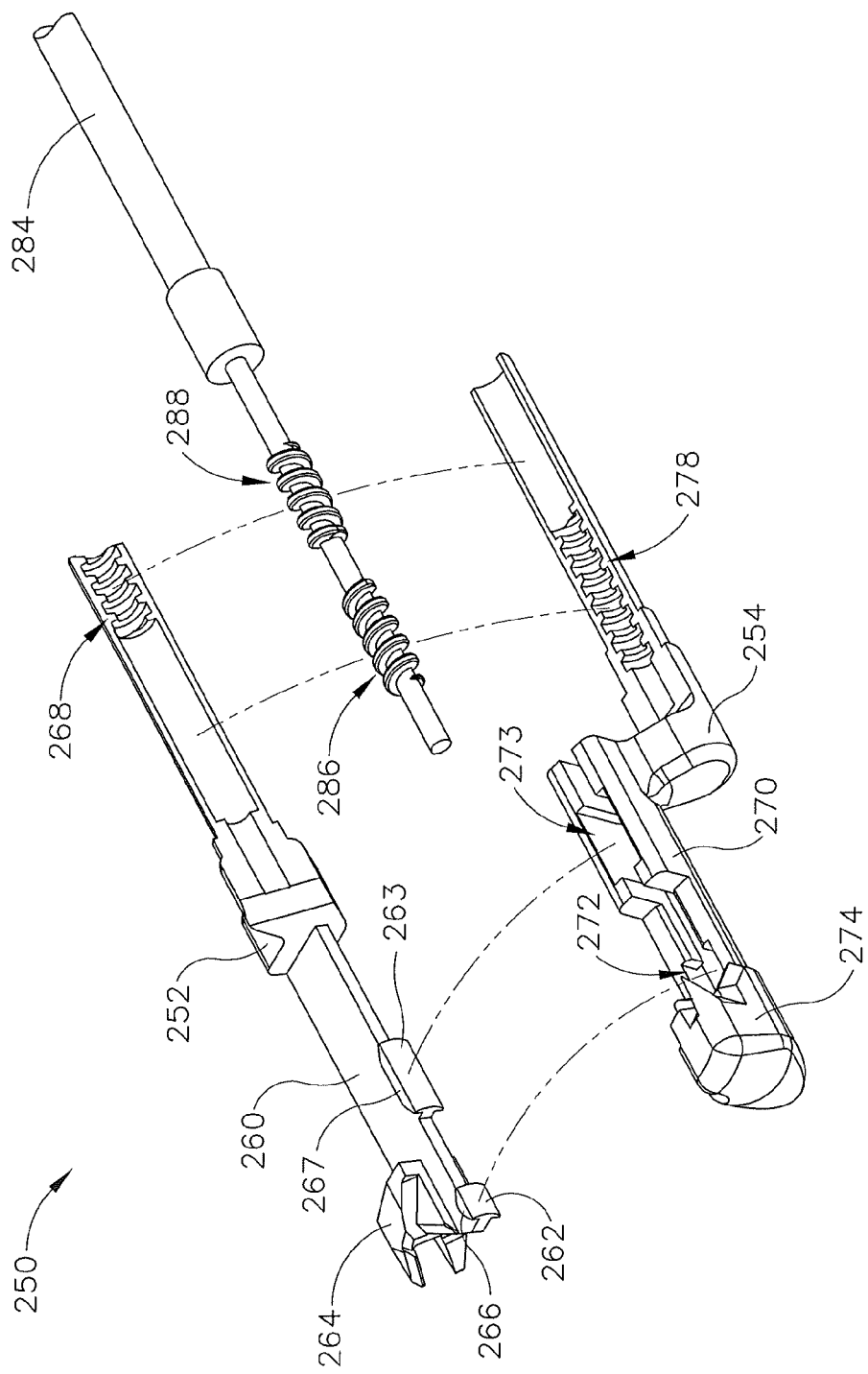
FIG. 16 depicts a partial exploded view of the second needle grasping arm of FIG. 13.

FIG. 16 shows exemplary features that may be used to provide the simultaneous opposing motion of jaws (260, 270) described above. In particular, FIG. 16 shows a drive shaft (284) that includes a first threaded section (286) and a second threaded section (288). Drive shaft (284) is coaxially positioned within sheath (280) and is rotatable within sheath (280). Drive shaft (284) is rotatably driven by motor (28) in handle portion (20). The threading of first threaded section (286) is oriented opposite to the threading of second threaded section (288), such that threaded sections (286, 288) have opposite pitches. The proximal portions of jaws (260, 270) together encompass the distal portion of drive shaft (284). In particular, the proximal portion of jaw (260) includes threading (268) that meshes with first threaded section (286); while the proximal portion of jaw (270) includes threading (278) that meshes with second threaded section (288). It should therefore be understood that threading (268) has a pitch that is opposite to the pitch of threading (278). It should also be understood that, due to the relationships and orientations of threaded sections (286, 288) and threading (268, 278), drive shaft (284) will cause jaws (260, 270) to simultaneously translate away from each other (FIG. 15A) when drive shaft (284) is rotated in one direction; while drive shaft (284) will cause jaws (260, 270) to simultaneously translate toward each other (FIG. 15B) when drive shaft (284) is rotated in the other direction.

In some settings, the rotational position of sheath (280) is fixed relative to shaft (100) when drive shaft (284) is rotated relative to shaft (100). Thus, sheath (280) substantially holds the rotational position of jaws (260, 270) when drive shaft (284) is rotated. In some other settings, sheath (280) and drive shaft (284) are rotated simultaneously relative to shaft (100). In some such instances, sheath (280) and drive shaft (284) are rotated in the same direction and at the same speed, such that drive shaft (284) and jaws (260, 270) are rotated in the same direction and at the same speed. Thus, the longitudinal positioning of jaws (260, 270) remains fixed during such rotation. As another merely illustrative variation, sheath (280) and drive shaft (284) may be rotated simultaneously relative to shaft (100), but at different speeds and/or in different directions. Such a scheme provides a rotation differential between jaws (260, 270) and drive shaft (284), such that jaws (260, 270) may open or close while second grasping arm (250) is simultaneously being rotated relative to shaft (100).

It should be understood that the opposing thread configuration described above may require relatively low torsional force to rotate drive shaft (284) to drive jaws (260, 270) toward and away from each other. It should also be understood that the opposing thread configuration described above may provide a relatively high holding force. For instance, when needle grasping features (264, 274) are driven toward each other to secure needle (50) as shown in FIG. 15B, and needle (50) is off-plane for whatever reason (e.g., incidentally oriented slightly obliquely relative to the longitudinal axis of shaft (100), etc.), the needle holding forces at grasping features (264, 274) may be self-reinforcing due to opposing forces provided through the opposing thread configuration described above, providing a mechanical advantage to urge needle (50) back into the desired planar orientation, even if tissue or some other structure is resisting such movement of needle into the desired planar orientation. Similarly, the opposing thread configuration described above may provide friction that acts as an anti-backup feature, substantially resisting inadvertent separation of grasping features (264, 274), thereby providing a very secure hold of needle (50).

Flanges (262, 263) may also include ramped interfaces with slot (261) to reduce the likelihood of jaws (260, 270) longitudinally separating while in the closed position shown in FIG. 15B. In FIG. 16, flange (262) has a ramped portion (266) extending outward along the perimeter edges of flange (262). Flange (263) is also configured with a ramped portion (267) extending outward along the perimeter edges of flange (263). Slot (261) on jaw (270) has a ramped portion extending inwardly along its sidewalls to correspond to the ramped portion (266, 267) of flanges (262, 263). Flanges (262, 263) and slot (261) may extend in another direction as will be apparent to one with ordinary skill in the art in view of the teachings herein. Ramped portions (266, 267) of flanges (262, 263) and slot (261) may interface to provide an additional interlocking interface between jaws (260, 270). Accordingly, when jaws (260, 270) are in a closed position to grasp needle (50), ramped portions (266, 267) provide additional forces to impinge against top edge (55) and bottom edge (57) of needle (50). Ramped portions (266, 267) may also include an elastic material to increase the friction between jaws (260, 270). Other suitable components that may be used to provide opposing motion of grasping features (264, 274) (e.g., a pinion with opposing racks, etc.) will be apparent to those of ordinary skill in the art in view of the teachings herein.

As noted above, drive shaft (284) may be selectively driven in either rotational direction by motor (28), such as in response to actuation of rocker (24). Sheath (280) may also be driven by motor (28). Alternatively, any other motive source and/or user input feature may be used. It should also be understood that, while drive shaft (284) rotates about an axis that is parallel to the axis of shaft (100), alternative drive systems that include a rotary member may provide rotation of such a rotary member about an axis that is not parallel to the axis of shaft (100). For instance, a pinion based drive system may provide rotation of a drive pinion about an axis that is perpendicular to the axis of shaft (100). Other suitable ways in which one or more components of second grasping arm (250) may be actuated will be apparent to those of ordinary skill in the art in view of the teachings herein.

1. Exemplary First Grasping Feature

Figure 17:
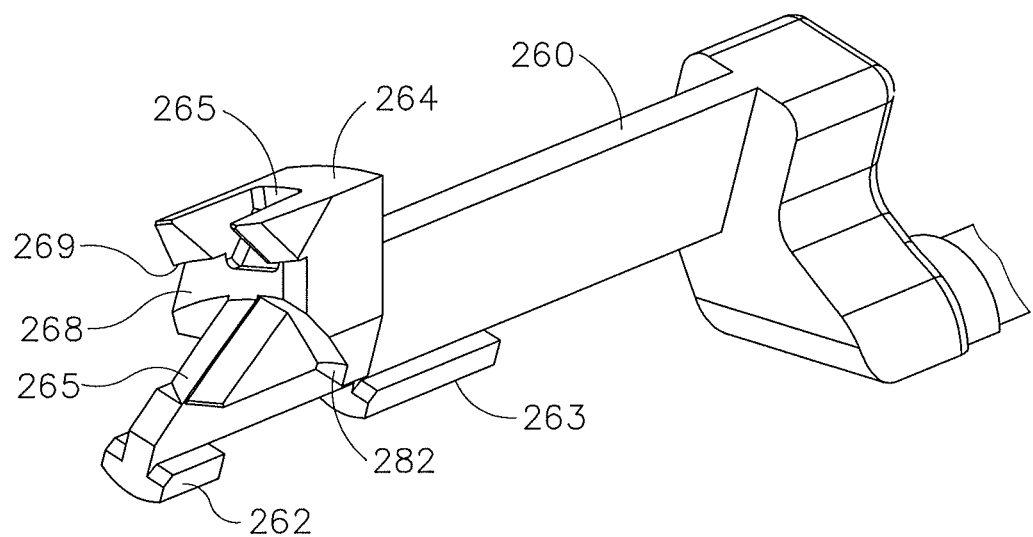
FIG. 17 depicts a partial perspective view of a first needle grasping feature of the second needle grasping arm of FIG. 13.
Figure 18:
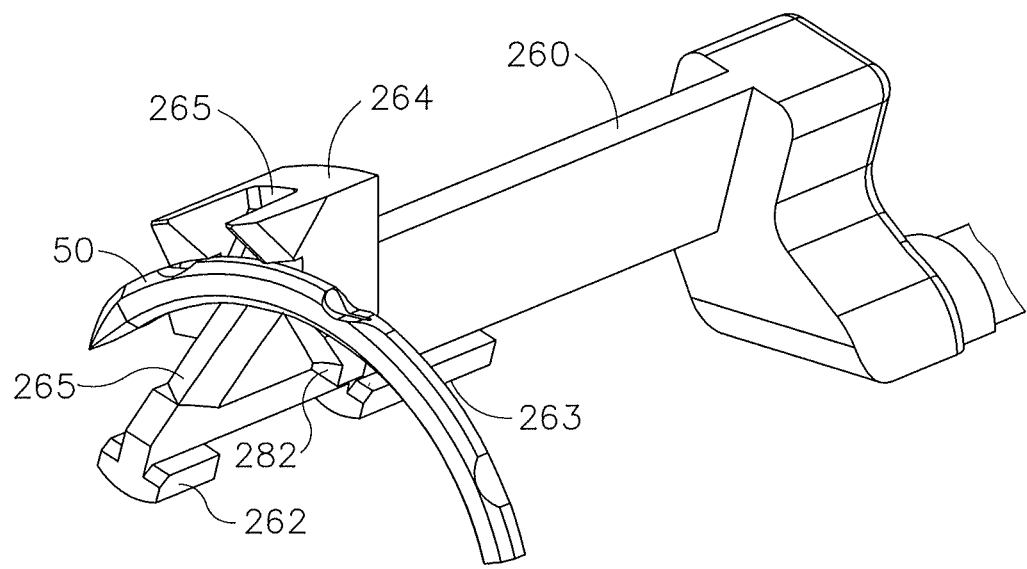
FIG. 18 depicts a partial perspective view of the first needle grasping feature of FIG. 17 engaged with the needle of FIG. 2.

FIGS. 17 and 18 show a more detailed view of first grasping feature (264) of first jaw (260). First grasping feature (264) includes chamfered lead-in surfaces (282), mating interfaces (268, 269), and ramp (265). First grasping feature (264) has chamfered lead-in surfaces (282) on the side surfaces to guide needle (50) into first grasping feature (264). Mating interface (269) extends horizontally from first grasping feature (264) to align with top edge (55) of needle (50). Mating interface (268) extends vertically from first grasping feature (264) to align with side edge (53) of needle (50). Ramp (265) interfaces with second grasping feature (274) to provide a more secure grip on needle (50). This is discussed in greater detail below.

If needle (50) is misaligned from arc path (68) about one or more axes (61, 63, 65) as needle (50) is passed from first grasping arm (210) to second grasping arm (250), chamfered lead-in surfaces (282), mating surfaces (268, 269), and ramp (265) work to realign and guide needle (50) into an aligned position in second grasping arm (250) as grasping features (264, 274) translate toward each other. For instance, if needle (50) is rolled about axis (61), mating surface (269) interfaces with top edge (55) of needle (50), mating surface (268) interfaces with side edge (53) of needle (50), and ramp (265) interfaces with bottom edge (57) of needle (50) to realign needle (50) about axis (61). Angled sides (41, 47) of needle (50) are adjacent to top edge (55) and side edge (53) to help guide needle (50) to mating surfaces (268, 269) in the event that needle (50) is rolled about axis (61). If needle (50) is pitched about axis (63) or yawed about axis (65), chamfered lead-in surfaces (282) guide needle (50) into first grasping feature (264) to realign needle (50) about axes (63, 65). Mating surfaces (268, 269) then cooperate with surfaces (276, 278) of second jaw (270), as will be described in greater detail below, to hold needle (50) in the aligned arc path (68) position in first grasping feature (264).

2. Exemplary Second Grasping Feature

Figure 19:
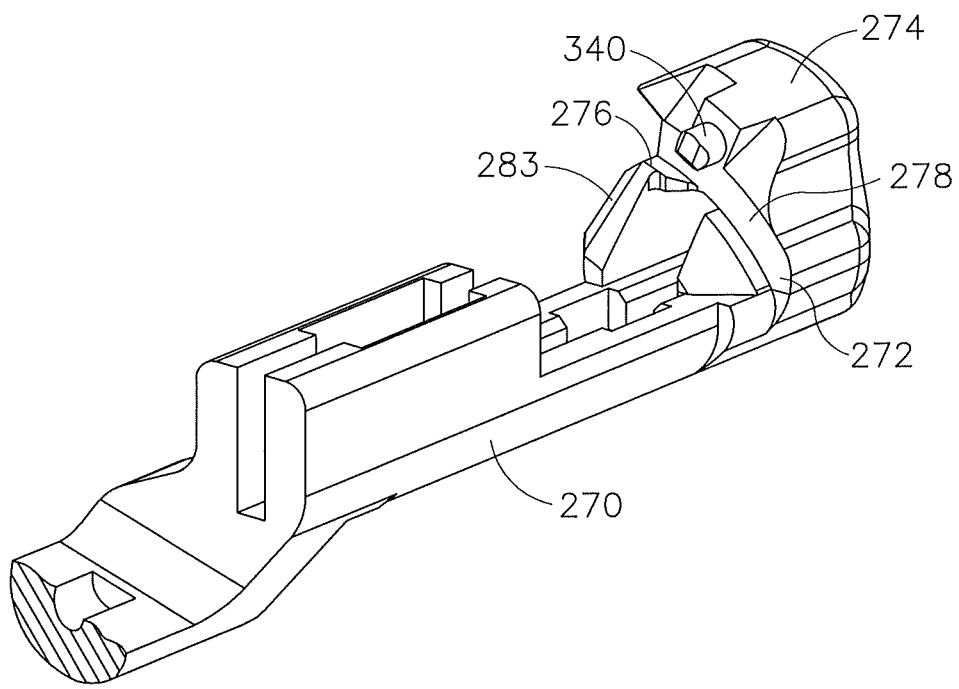
FIG. 19 depicts a partial perspective view of a second needle grasping feature of the second needle grasping arm of FIG. 13.
Figure 20:
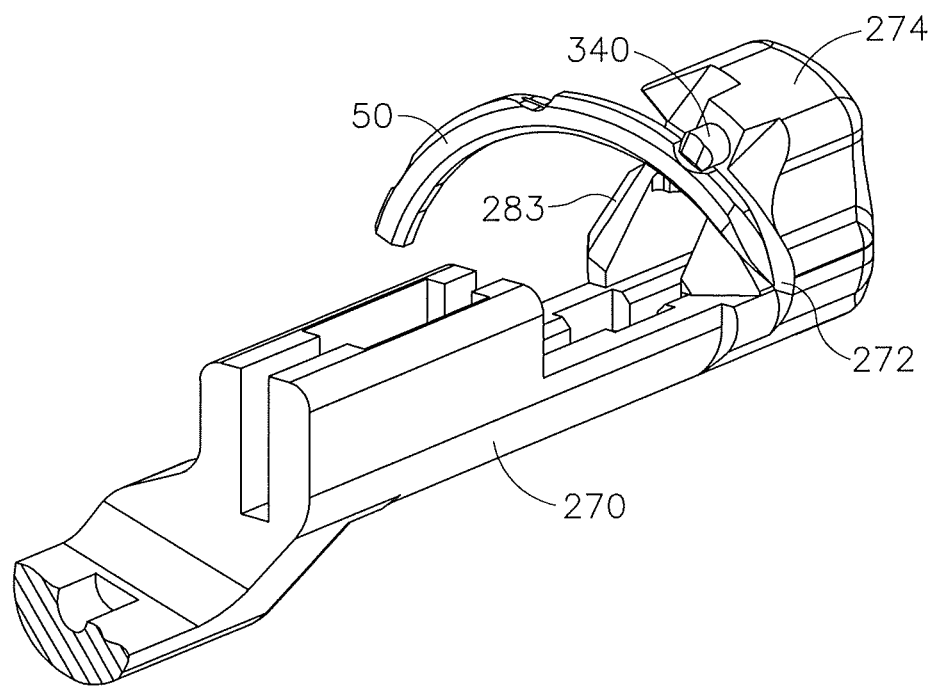
FIG. 20 depicts a partial perspective view of the second needle grasping feature of FIG. 19 engaged with the needle of FIG. 2.

FIGS. 19 and 20 show a more detailed view of second grasping feature (274) of second jaw (270). Second grasping feature (274) includes chamfered lead-in surfaces (283), mating interfaces (276, 278), and location feature (340). Second grasping feature (274) has chamfered lead-in surfaces (283) on the side surfaces to guide needle (50) into second grasping feature (274). Mating interface (276) extends horizontally from second grasping feature (274) to align with bottom edge (57) of needle (50). Mating interface (278) extends vertically from second grasping feature (274) to align with side edge (53) of needle (50). Locating feature (340) extends proximally from the top portion of second grasping feature (274). As shown in FIG. 20, locating feature (340) has a cylindraceous configuration to correspond to grasping region (56) of needle (50). However, location feature (340) and grasping region (56) may be any other shape as will be apparent to one with ordinary skill in the art in view of the teachings herein. Locating feature (340) also has a chamfered free end. Of course, location feature (340) and grasping region (56) may have any other suitable configuration as will be apparent to one with ordinary skill in the art in view of the teachings herein.

As needle (50) is passed from first grasping arm (210) to second grasping arm (250), needle (50) proceeds into second grasping arm (250) until location feature (340) is generally aligned with grasping region (56) of needle (50). If needle (50) is aligned with arc path (68) yet is improperly positioned along arc path (68), the configurations of location feature (340) and grasping region (56) cooperate to properly position needle (50) along arc path (68) as jaws (260, 270) are closed together. Ramp (265) may further cooperate with bottom edge (57) of needle (50) to assist in driving grasping region (56) into a substantially centered position adjacent to location feature (340).

If needle (50) is misaligned from arc path (68) about one or more axes (61, 63, 65) as needle (50) is passed to second grasping arm (250), chamfered lead-in surfaces (283) and mating surfaces (276, 278) work to realign and guide needle (50) into an aligned position in second grasping arm (250) as grasping features (264, 274) translate toward each other. For instance, if needle (50) is rolled about axis (61), mating surface (276) interfaces with bottom edge (57) of needle (50) and mating surface (278) interfaces with side edge (51) of needle (50) to realign needle (50) about axis (61). Angled sides (43, 45) of needle (50) are adjacent to bottom edge (57) and side edge (51) to help guide needle (50) to mating surfaces (276, 278) in the event that needle (50) is rolled about axis (61). If needle (50) is pitched about axis (63) or yawed about axis (65), chamfered lead-in surfaces (283) guide needle (50) into second grasping feature (274) to realign needle (50) about axes (63, 65). Mating surfaces (276, 278) then cooperate with surfaces (268, 269) of first jaw (260) to hold needle (50) in the aligned arc path (68) position in second grasping feature (274).

As shown in FIGS. 15A-15B, first grasping feature (264) presents a U-shaped profile (turned on its side in FIGS. 15A-15B). Mating surface (269) forms one leg of the U-shaped configuration, mating surface (268) forms the base of the U-shaped configuration, and ramp (265) forms the other leg of the U-shaped configuration. Second grasping feature (274) has a corresponding but oppositely oriented U-shaped profile. Locating feature (340) forms one leg of the U-shaped configuration, mating surface (278) forms the side of the U-shaped configuration, and mating surface (276) forms the other leg of the U-shaped configuration. The U-shaped profiles of first grasping feature (264) and second grasping feature (274) are substantially separated when second grasping arm (250) is in an open configuration as shown in FIG. 15A. The U-shaped profiles then substantially overlap when second grasping arm (250) is in a closed configuration as shown in FIG. 15B. The overlap of the U-shaped configurations may assist in providing a substantially secure grip of needle (50) by second grasping arm (250).

As shown in FIG. 21 second grasping feature (274) of the present example also has a needle protection portion (272). Needle protection portion (272) extends past tip (52) of needle (50) from the lower portion of second grasping feature (274) when second grasping arm (250) grasps needle (50). When needle (50) is passed from first grasping arm (210) to second grasping arm (250), and while needle (50) is grasped by second grasping arm (250), tip (52) of needle (50) lies within needle protection portion (272). This prevents tip (52) of needle (50) from inadvertently puncturing or tearing tissue while needle (50) is grasped by second grasping arm (25), yet still allows visualization of tip (52) while needle (50) is grasped by second grasping arm (25).

III. Exemplary Method of Operation

Figure 22A:
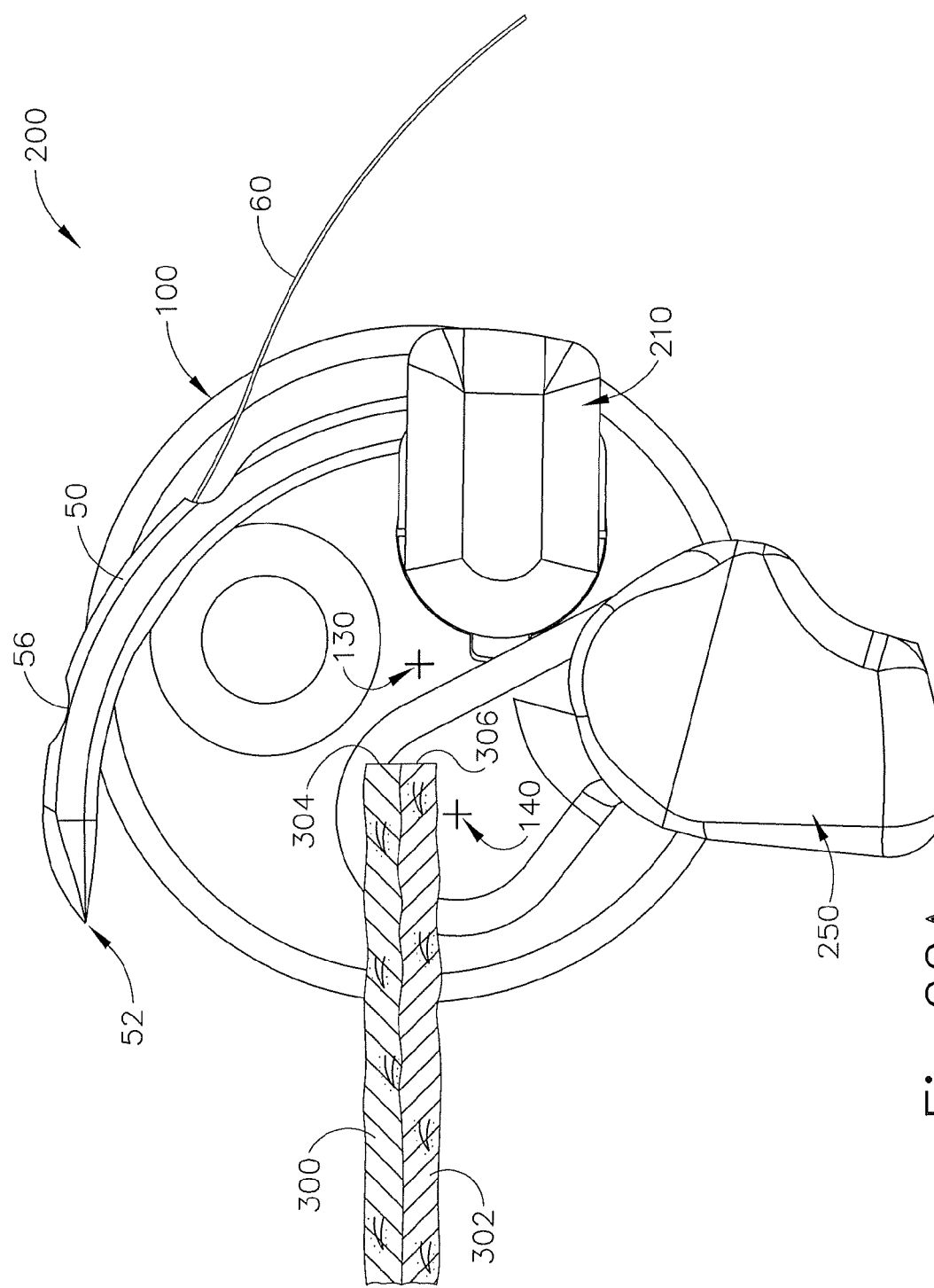
FIG. 22A depicts an end view of the end effector and needle of FIG. 4A, during an exemplary first stage of operation.

FIGS. 22A-22H depict a merely exemplary method for using surgical instrument (10). In particular, FIG. 22A shows end effector (200) positioned adjacent to apposed layers (300, 302) of tissue. End effector (200) is positioned such that the longitudinal axis (130) of shaft (100) is substantially parallel to the outer edges (304, 306) of tissue layers (300, 302). In this sense, "substantially parallel" simply means that end effector (200) is oriented in relation to tissue layers (300, 302) in a manner sufficient to enable needle (50) to be passed through tissue layers (300, 302). It should therefore be understood that longitudinal axis (130) need not necessarily be truly parallel with outer edges (304, 306), though longitudinal axis (130) may in fact be truly parallel with outer edges (304, 306) in some instances. It should also be understood that instrument (10) and needle (50) may be used to secure tissue together in an edge-to-edge arrangement rather than securing apposed layers (300, 302) as shown. Other suitable settings in which instrument (10) and needle (50) may be used will be apparent to those of ordinary skill in the art in view of the teachings herein. It should also be understood that the curved configuration of needle (50) may provide a more intuitive operation for the surgeon than a straight needle would, such as by providing better predictability for where sharp tip (52) will come through tissue.

Figure 22B:
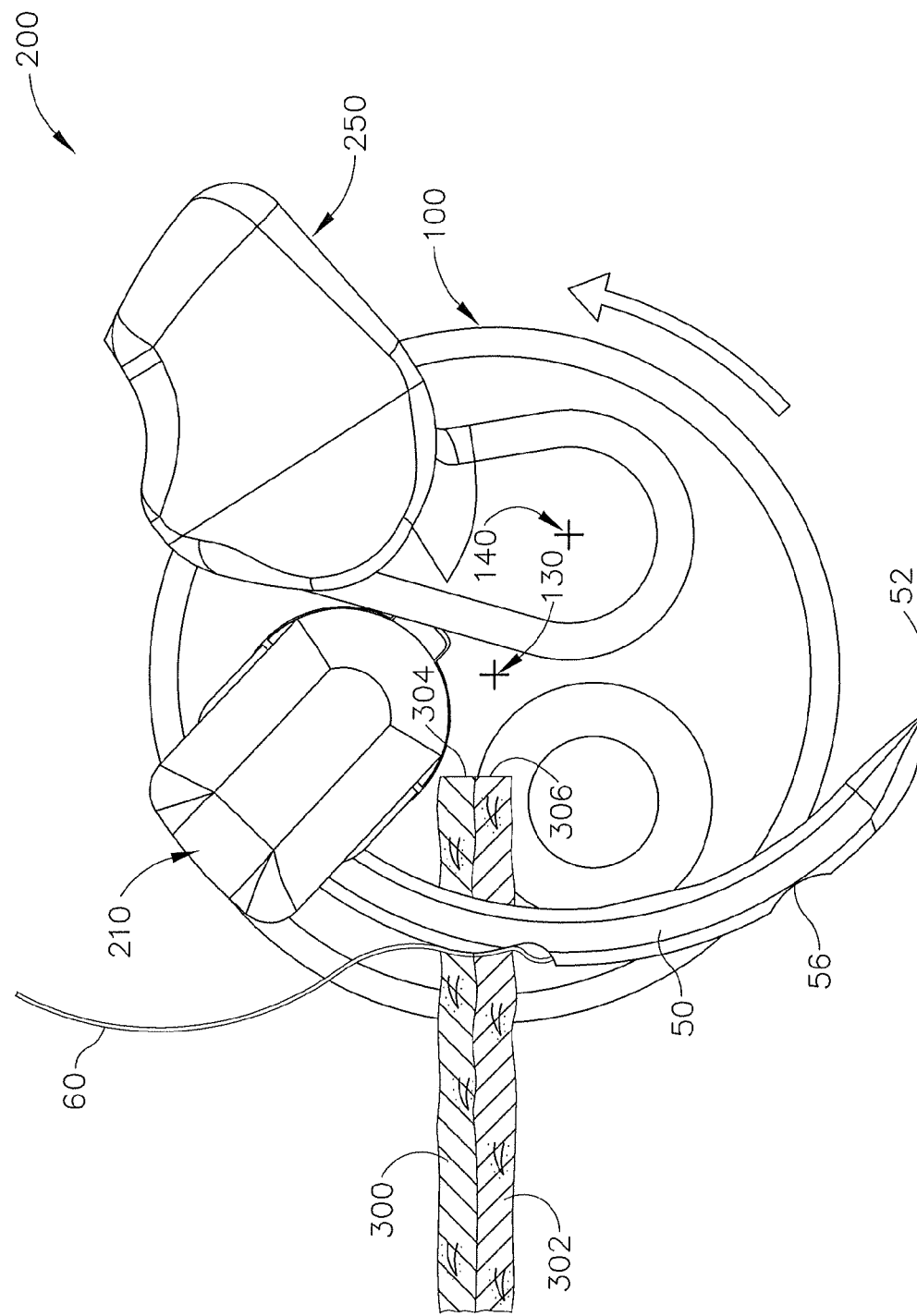
FIG. 22B depicts an end view of the end effector and needle of FIG. 4A, during an exemplary second stage of operation.

As shown in FIG. 22A, first grasping arm (210) is securely holding needle (50), with sharp tip (52) exposed. In particular, grasping portions (224, 234) of jaws (220, 230) hold needle (50) at grasping region (56). Needle (50) is oriented along a plane that is substantially transverse to longitudinal axis (130). Once end effector (200) has been positioned as shown in FIG. 22A, the entire instrument (10) is rotated about longitudinal axis (130) to drive sharp tip (52) through tissue layers (300, 302), as shown in FIG. 22B. In the example shown, the rotational direction for instrument (10) is counterclockwise viewed from the distal end toward the proximal end, though it should be understood that instrument (10) may be rotated clockwise instead (e.g., depending on the orientation of sharp tip (52)). During the transition from the position of FIG. 22A to the position of FIG. 22B, the rotational position of grasping arms (210, 250) relative to shaft (100) remains fixed, such that grasping arms (210, 250) rotate unitarily with shaft (100) about longitudinal axis (130). The longitudinal position of jaws (220, 230, 260, 270) also remains fixed during this transition. As can also be seen in FIG. 22B, needle (50) has started to pull suture (60) through tissue layers (300, 302) at this stage. It should be understood that, in the stages shown in FIGS. 22A-22B, grasping arms (210, 250) and needle (50) are in the same rotational positions relative to shaft (100) as shown in FIG. 4A. It should also be noted that the configuration of end effector (200) and needle (50) may provide the surgeon with enhanced visibility of sharp tip (52) exiting tissue layers (300, 302) during the transition from FIG. 22A to FIG. 22B, particularly with arm (250) being rotated out of the way at this stage.

Figure 22C:
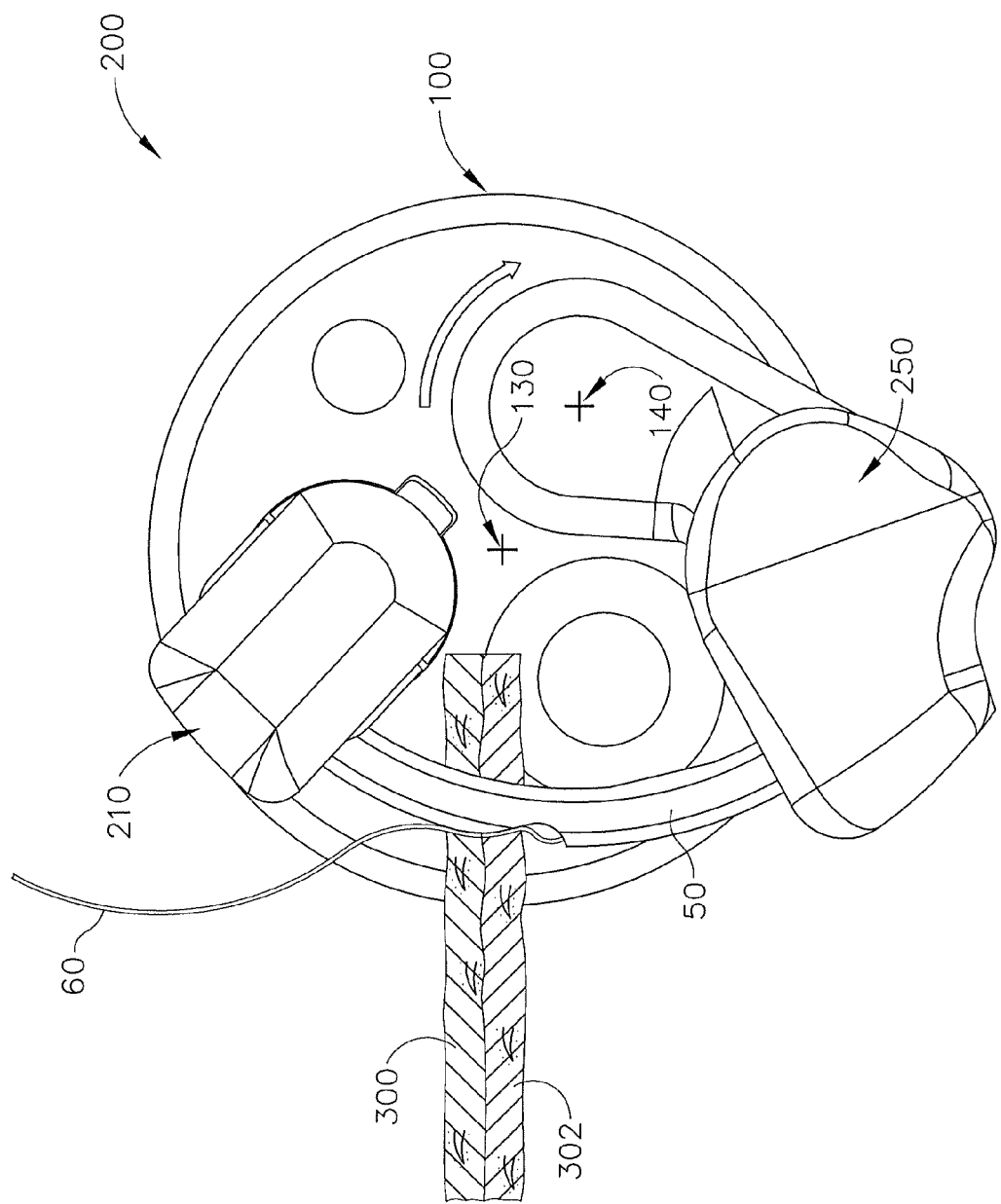
FIG. 22C depicts an end view of the end effector and needle of FIG. 4A, during an exemplary third stage of operation.

After needle (50) has been driven at least partially through tissue layers (300, 302), second grasping arm (250) is rotated about its own axis (140) toward needle (50) as shown in FIG. 22C. Such rotation is provided by rotating sheath (280) relative to shaft (100). The rotational position of shaft (100) relative to axis (130) remains fixed during the transition from the configuration shown in FIG. 22B to the configuration shown in FIG. 22C. It should be understood that, in the stage shown in FIG. 22C, grasping arms (210, 250) and needle (50) are in the same rotational positions relative to shaft (100) as shown in FIG. 4B.

In some versions, jaws (260, 270) are already opened (as shown in FIG. 15A) by the time second grasping arm (250) starts rotating from the position shown in FIG. 22B to the position shown in FIG. 22C. In some other versions, jaws (260, 270) are actively opened during the transition from the position shown in FIG. 22B to the position shown in FIG. 22C, such that jaws (260, 270) are fully open by the time second grasping arm (250) reaches the position shown in FIG. 22C. Once second grasping arm (250) reaches the position shown in FIG. 22C, jaws (260, 270) close (as shown in FIG. 15B) to grasp needle (50) at grasping region (58) with grasping features (264, 274). In addition, jaws (220, 230) open (as shown in FIG. 7A) to release needle (50) from grasping features (224, 234) at grasping region (56). In some versions, jaws (260, 270) close to grasp needle (50) at substantially the same time as jaws (220, 230) open to release needle (50). In some other versions, jaws (220, 230) do not open to release needle (50) until jaws (260, 270) have closed to grasp needle (50). Various suitable timing schemes and ways in which such schemes may be carried out will be apparent to those of ordinary skill in the art in view of the teachings herein.

As needle (50) is passed from first grasping arm (210) to second grasping arm (250), needle (50) may deviate from arc path (68) (e.g., about one or more of axes (61, 63, 65), etc.) from passing through tissue (300, 302). Mating surfaces (268, 269, 276, 278) on second grasping arm (250) interface with top (55), sides (51, 53), and bottom (57) edges of needle (50) to align needle (50) about axes (61, 63, 65) as needle (50) is grasped by second grasping arm (250). Chamfered lead-in surfaces (282, 283) of second grasping arm (250) guide needle (50) into an aligned position as needle (50) is grasped by second grasping arm (250). Location feature (340) aligns above grasping region (56) of needle (50) to align needle (50) to the proper position along the arc path (68) of needle (50) relative to second grasping arm (250).

Figure 22D:
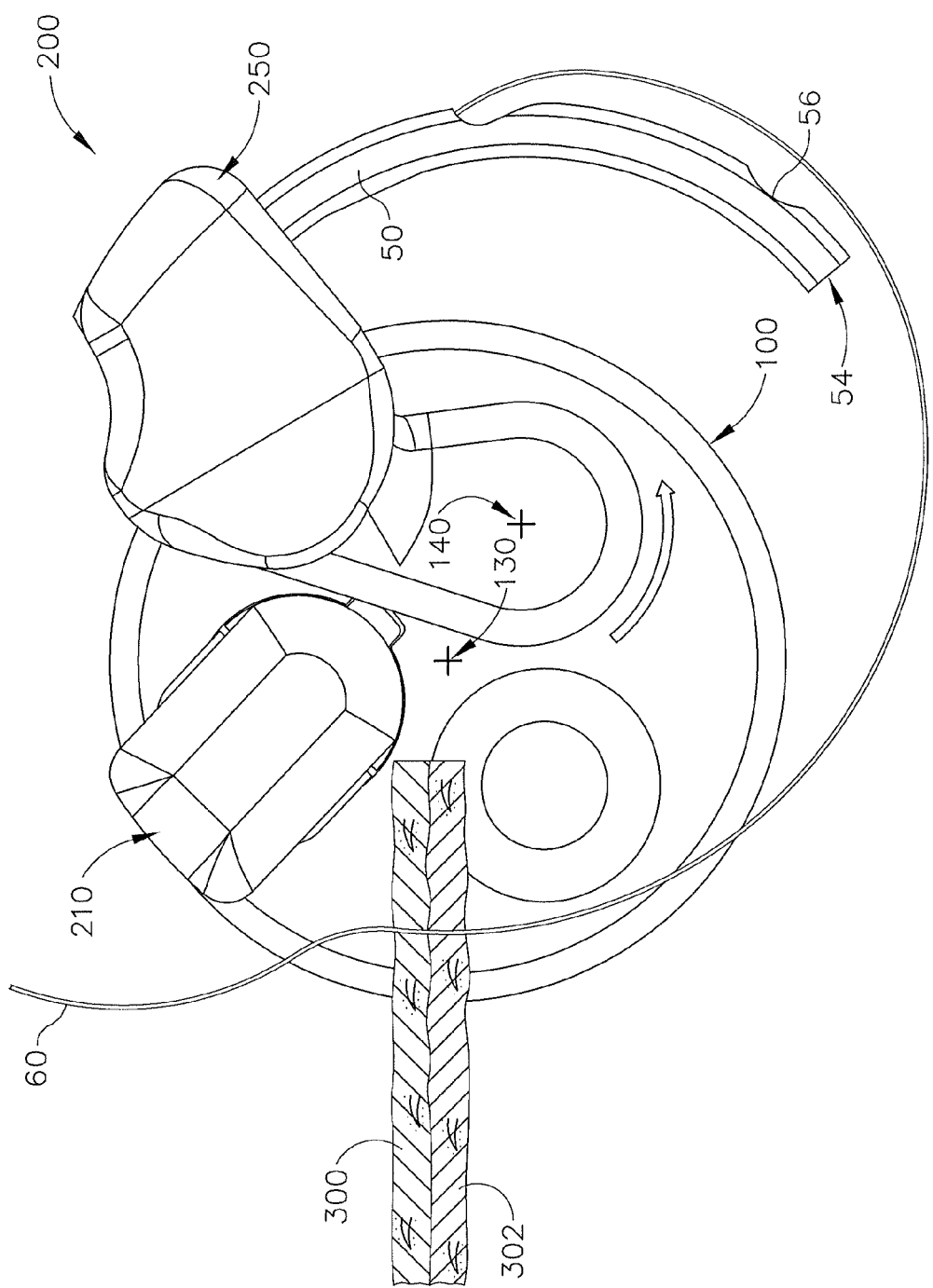
FIG. 22D depicts an end view of the end effector and needle of FIG. 4A, during an exemplary fourth stage of operation.

Once control of needle (50) has been effectively passed from grasping arm (210) to grasping arm (250), grasping arm (250) is rotated about axis (140) to the position shown in FIG. 22D. Such rotation is provided by once again rotating sheath (280) relative to shaft (100). The rotational position of shaft (100) relative to axis (130) continues to be fixed during the transition from the configuration shown in FIG. 22C to the configuration shown in FIG. 22D. It should be understood that, in the stage shown in FIG. 22D, grasping arms (210, 250) and needle (50) are in the same rotational positions relative to shaft (100) as shown in FIG. 4C. As can also be seen in FIG. 22D, grasping arm (250) pulls suture (60) through tissue layers (300, 302) during the transition from FIG. 22C to FIG. 22D.

Figure 22E:
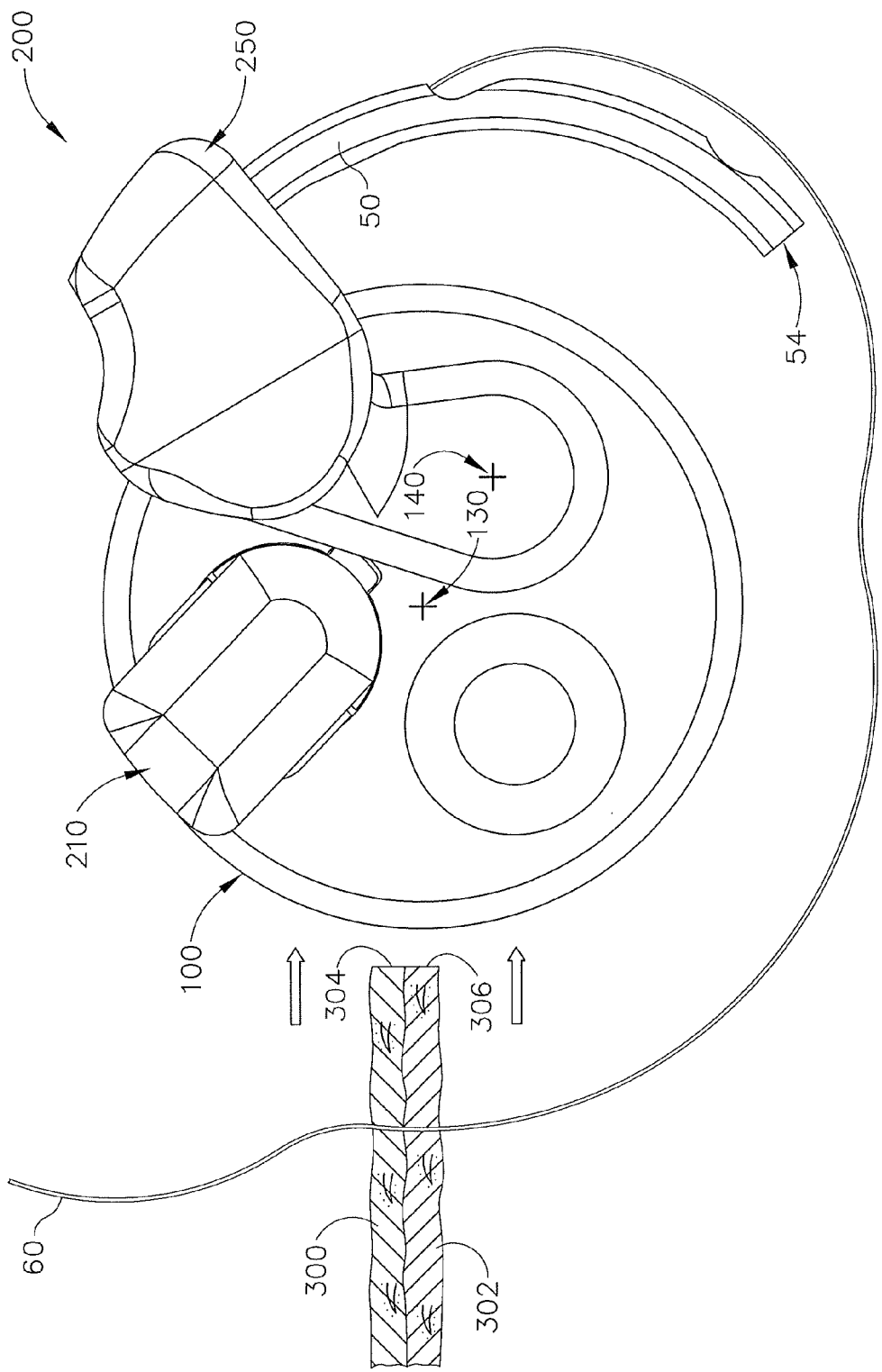
FIG. 22E depicts an end view of the end effector and needle of FIG. 4A, during an exemplary fifth stage of operation.

After reaching the configuration shown in FIG. 22D, the surgeon pulls the entire end effector (200) away from tissue layers (300, 302). Needle protection portion (272) on second grasping arm (250) extends past tip (52) of needle (50). This ensures that needle (50) does not cut or puncture any other tissue or organs near the operating area when the surgeon pulls end effector (200) away from tissue layers (300, 302). End effector (200) is pulled away along a path that is substantially transverse to axis (130), as shown in FIG. 22E. It should be understood that this path may be oblique relative to axis (130) and/or edges (304, 306), helical, and/or of any other suitable configuration. It should also be understood that neither arm (210, 250) is rotated relative to shaft (100) in the present example during the transition from the position shown in FIG. 22D to the position shown in FIG. 22E. Thus, in the stage shown in FIG. 22E, grasping arms (210, 250) and needle (50) are still in the same rotational positions relative to shaft (100) as shown in FIG. 4C. In moving instrument (10) away from tissue layers (300, 302) during the transition to the position shown in FIG. 22E, suture (60) is pulled further through tissue layers (300, 302).

With end effector (200) positioned sufficiently away from tissue layers (300, 302), second grasping arm (250) is rotated about axis (140) to the position shown in FIG. 22F. The rotational position of shaft (100) relative to axis (130) remains fixed during the transition from the configuration shown in FIG. 22E to the configuration shown in FIG. 22F. It should be understood that, in the stage shown in FIG. 22F, grasping arms (210, 250) and needle (50) are in the same rotational positions relative to shaft (100) as shown in FIG. 4B. End effector (200) is positioned far enough away from tissue layers (300, 302) during the transition from the position shown in FIG. 22E to the position shown in FIG. 22F such that blunt end (54) of needle (50) does not touch tissue layers (300, 302). The rotation of second grasping arm (250) to the position shown in FIG. 22F places grasping region (58) of needle (50) back between grasping portions (224, 234) of jaws (220, 230).

In some versions, jaws (220, 230) are already opened (as shown in FIG. 7A) by the time second grasping arm (250) starts rotating from the position shown in FIG. 22E to the position shown in FIG. 22F. In some other versions, jaws (220, 230) are actively opened during the transition from the position shown in FIG. 22E to the position shown in FIG. 22F, such that jaws (220, 230) are fully open by the time second grasping arm (250) reaches the position shown in FIG. 22F. Once second grasping arm (250) reaches the position shown in FIG. 22F, jaws (220, 230) close (as shown in FIG. 7B) to grasp needle (50) at grasping region (56) with grasping portions (224, 234). In addition, jaws (260, 270) open (as shown in FIG. 15A) to release needle (50) from grasping portions (264, 274) at grasping region (58). In some versions, jaws (220, 230) close to grasp needle (50) at substantially the same time as jaws (260, 270) open to release needle (50). In some other versions, jaws (260, 270)

do not open to release needle (50) until jaws (220, 240) have closed to grasp needle (50). Various suitable timing schemes and ways in which such schemes may be carried out will be apparent to those of ordinary skill in the art in view of the teachings herein.

As needle (50) is passed from second grasping arm (250) to first grasping arm (210), needle (50) may be misaligned while being pulled, such that needle (50) needle (50) may deviate from arc path (68) (e.g., about one or more of axes (61, 63, 65), etc.). Mating surfaces (226, 228, 236, 238) on first grasping arm (210) interface with top (55), sides (51, 53), and bottom (57) edges of needle (50) to align needle (50) about axes (61, 63, 65) as needle (50) is grasped by first grasping arm (250). Chamfered lead-in surfaces (242, 243) of first grasping arm (210) guide needle (50) into an aligned position as needle (50) is grasped by first grasping arm (210). Location feature (240) aligns above grasping region (58) of needle (50) to align needle (50) to the proper position along the arc path (68) of needle (50) relative to first grasping arm (210).

Figure 22G:
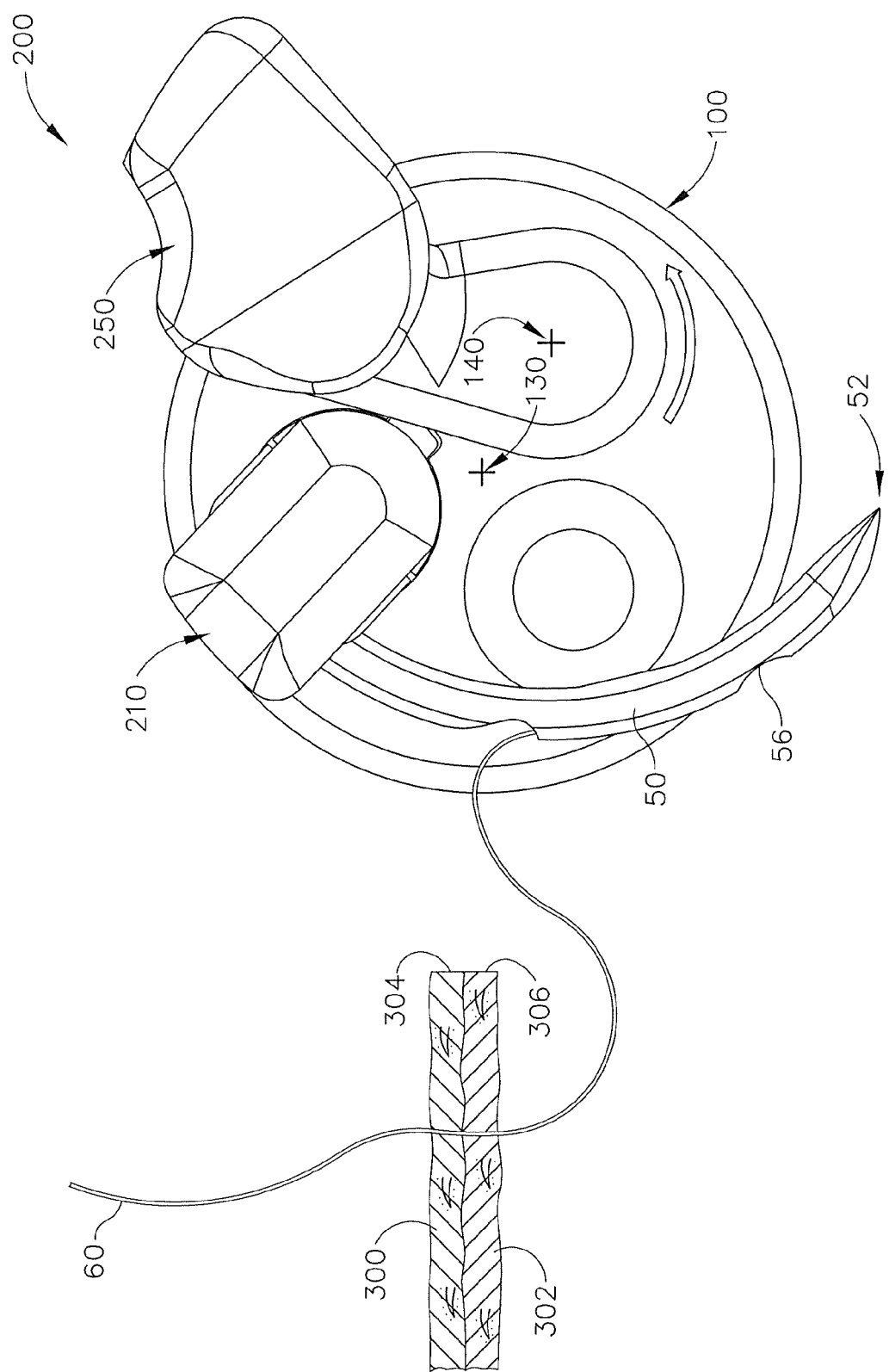
FIG. 22G depicts an end view of the end effector and needle of FIG. 4A, during an exemplary seventh stage of operation.

Once control of needle (50) has been effectively passed from grasping arm (250) back to grasping arm (210), grasping arm (250) is rotated about axis (140) to the position shown in FIG. 22G. Such rotation is provided by once again rotating sheath (280) relative to shaft (100). The rotational position of shaft (100) relative to axis (130) continues to be fixed during the transition from the position shown in FIG. 22F to the position shown in FIG. 22G. It should be understood that, in the stage shown in FIG. 12G, grasping arms (210, 250) and needle (50) are in the same rotational positions relative to shaft (100) as shown in FIG. 4A.

Figure 22H:
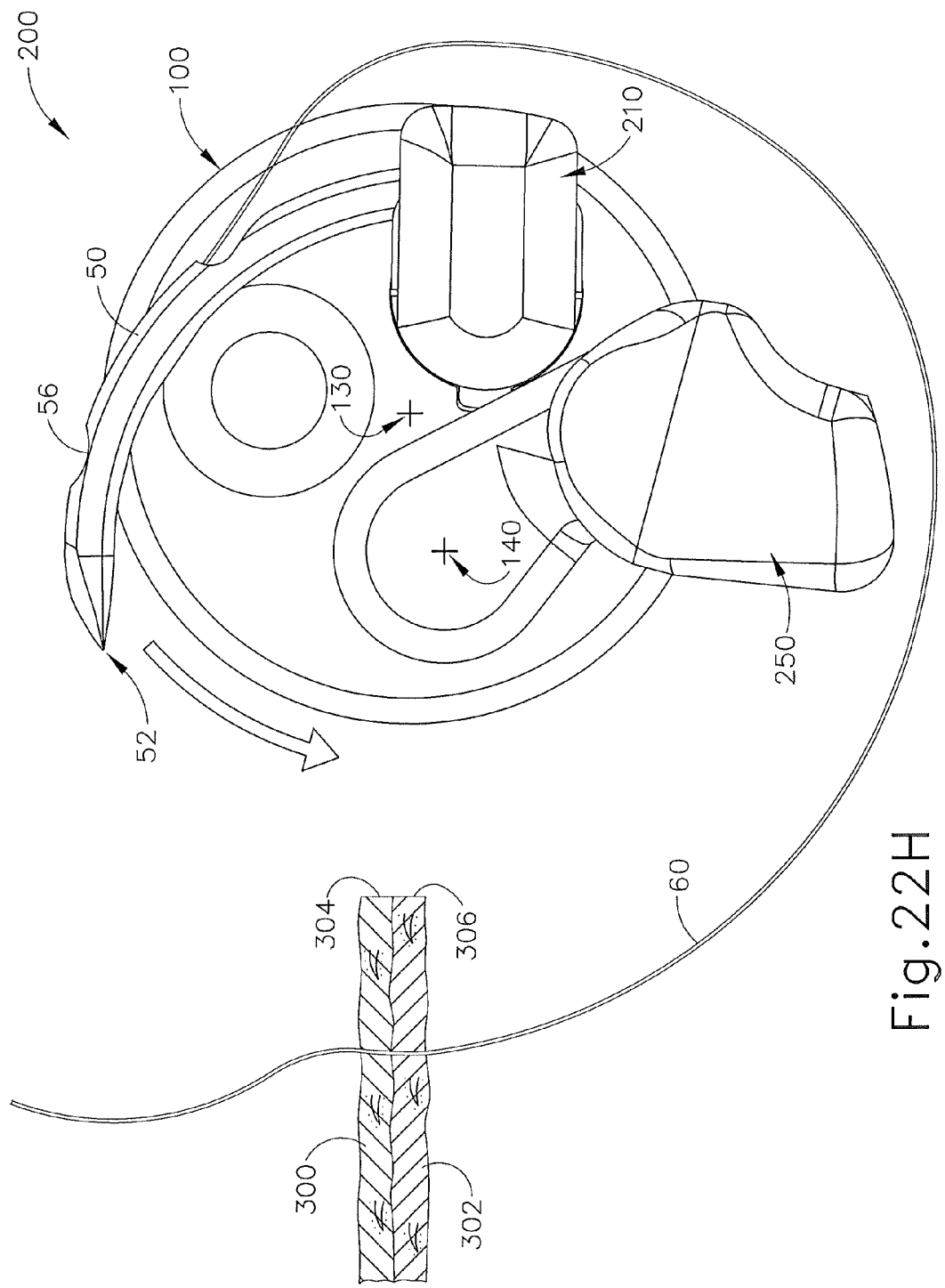
FIG. 22H depicts an end view of the end effector and needle of FIG. 4A, during an exemplary eighth stage of operation.

Once grasping arm (250) has been rotated away from needle (50) as shown in FIG. 22G, the entire instrument (10) is once again rotated about longitudinal axis (130) to position sharp tip (52) above tissue layers (300, 302), as shown in FIG. 22H. In the example shown, the rotational direction for instrument (10) is again counterclockwise viewed from the distal end toward the proximal end, though it should be understood that instrument (10) may be rotated clockwise instead (e.g., depending on the orientation of sharp tip (52)). During this transition, the rotational position of grasping arms (210, 250) relative to shaft (100) remains fixed, such that grasping arms (210, 250) rotate unitarily with shaft (100) about longitudinal axis (130). The longitudinal position of jaws (220, 230, 260, 270) also remains fixed during this transition. In the stage shown in FIG. 22H, grasping arms (210, 250) and needle (50) remain in the same rotational positions relative to shaft (100) as shown in FIG. 4A.

Having reached the configuration shown in FIG. 22H, end effector (200) may be moved back toward tissue layers (300, 302), such as along a path transverse to axis (130), to again reach the position shown in FIG. 22A. The above described cycle may then be repeated as many times as desired until an appropriate number of stitches have been made through tissue layers (300, 302). The free end of suture (50) may then be knotted, clipped, or otherwise secured.

It should be understood that instrument (10) may be advanced distally or proximally along axis (130) in each stitching cycle, each stitching cycle being represented by the succession of stages depicted in FIGS. 22A-22H. For instance, instrument (10) may be advanced distally or proximally along axis (130) during the transition from the position shown in 22E to the position shown in 22F. As another merely illustrative example, instrument (10) may be advanced distally or proximally along axis (130) during the transition from the position shown in 22G to the position shown in 22H. Other suitable stages at which instrument (10) may be advanced distally or proximally will be apparent to those of ordinary skill in the art in view of the teachings herein. It should be understood that the distance of each incremental distal or proximal movement of instrument (10) during successive stitching cycles may be selected based on a desired stitch density along the length of the tissue being sutured. It should also be understood that, once stitching is complete, suture (60) may define a generally helical path through tissue layers (300, 302). Other suitable ways in which instrument (10) may be used will be apparent to those of ordinary skill in the art in view of the teachings herein.

As should be apparent to those of ordinary skill in the art, needle (50) of the present example orbits about axis (140), which is offset from axis (130) of shaft (100) in the present example. This may enable needle (50) to travel about an arc having a radius that is greater than the radius of a trocar through which shaft (100) is inserted. In other words, the circumferential path of needle (50) need not be limited to the circumference of the trocar through which shaft (100) is inserted when the orbital axis of needle (50) is offset from axis (130) of shaft (100). Thus, the configuration of end effector (200) in the present example may permit a larger radius needle to be used, and larger stitches to be made, than what would be permitted if the orbital motion of needle (50) were centered about axis (130) of shaft (100). In some other versions, needle (50) does move in an orbital fashion about axis (130) of shaft (100).

While terms such as "clockwise" and "counterclockwise" have been used to describe directions of rotational movement during exemplary uses of end effectors (200, 400), it should be understood that these specific rotational directions are being provided only in reference to the examples depicted in the drawings. It is contemplated that rotational movement may be provided in directions opposite to those used above. Therefore, use of the terms "clockwise" and "counterclockwise" in the above examples should not be viewed as limiting in any way.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a shaft, wherein the shaft has a distal end;
   (b) a suture needle defining a length, wherein the suture needle comprises an exterior surface defining a preselected cutout; and
   (c) an end effector located at the distal end of the shaft, wherein the end effector comprises a first needle grasping arm, wherein the first needle grasping arm comprises:
      (i) a first needle grasping member, wherein the first needle grasping member has a needle receiving side, and
      (ii) a second needle grasping member, wherein the second needle grasping member comprises a needle receiving side and a location feature, wherein the first needle grasping member and the second needle grasping member are configured to translate toward each other to grasp the suture needle,
   wherein the first and second needle grasping members are operable to cooperatively align the suture needle along an arc path by positioning the suture needle about a roll axis, a pitch axis, and a yaw axis when the first and second needle grasping members translate toward each other to grasp the suture needle;
   wherein the first and second needle grasping members are further operable to correct at least some deviations of the suture needle about the roll axis, pitch axis, and yaw axis when the first and second needle grasping members translate toward each other to grasp the suture needle;
   wherein the location feature defines an axis that is oblique or orthogonal to a plane defined by the arc path, wherein the location feature is configured to extend at least partially through the preselected cutout of the suture needle at preselected discrete points along the length of the suture needle thereby contacting a portion of the exterior surface defining the preselected cutout to prevent the suture needle from traveling along the arc path relative to the location feature;
   wherein the first needle grasping member further comprises surfaces that are configured to interface with surfaces of the suture needle to rotate the suture needle relative to the first needle grasping member as the first and second needle grasping members translate toward each other; and
   wherein the first and second needle grasping members are operable to cooperatively grasp and release the suture needle such that the end effector is operable to selectively pass the suture needle between the first needle grasping arm and a second needle grasping arm.

2. The apparatus of claim 1, wherein the first needle grasping member further comprises chamfered surfaces on the needle receiving side of the first needle grasping member, wherein the chamfered surfaces on the needle receiving side of the first needle grasping member are configured to align the suture needle along the arc path to guide the suture needle relative to the first needle grasping member.

3. The apparatus of claim 2, wherein the needle receiving side of the second needle grasping member further comprises chamfered surfaces, wherein the chamfered surfaces on the needle receiving side of the second needle grasping member are configured to align the suture needle along the arc path to guide the suture needle relative to the second needle grasping member.

4. The apparatus of claim 1, wherein the surfaces of the first needle grasping member are configured to interface with top and side surfaces of the suture needle.

5. The apparatus of claim 1, wherein the second needle grasping member further comprises surfaces that are configured to interface with surfaces of the suture needle to rotate the suture needle about the roll axis and the yaw axis relative to the second needle grasping member as the first and second needle grasping members translate toward each other.

6. The apparatus of claim 5, wherein the surfaces of the second needle grasping member are configured to interface with side and bottom surfaces of the suture needle.

7. The apparatus of claim 5, wherein the first needle grasping member further comprises a ramp declining toward a plane defined by the arc path of the needle, wherein the ramp is configured to push the suture needle toward the location feature when the first needle grasping member and the second needle grasping member translate toward each other.

8. The apparatus of claim 1, wherein the location feature comprises at least one chamfered lead-in surface.

9. The apparatus of claim 1, wherein the location feature is substantially cylindrical.

10. The apparatus of claim 1, wherein the shaft and the end effector are dimensioned to fit through a surgical trocar.

11. The apparatus of claim 1, further comprising a handle assembly positioned at a proximal end of the shaft, wherein the handle assembly is operable to selectively activate the first and second needle grasping members.

12. The apparatus of claim 1, wherein the first needle grasping member is slidably coupled with the second needle grasping member.

13. The apparatus of claim 12, wherein the first needle grasping member comprises a linearly movable first jaw, wherein the second needle grasping member comprises a linearly movable second jaw, wherein the first and second jaw are linearly moveable in opposing directions along a common axis.

14. The apparatus of claim 13, wherein the first jaw comprises a U-shaped configuration, wherein the second jaw comprises a U-shaped configuration, wherein at least a portion of the U-shaped configuration of the first jaw is configured to overlap with at least a portion of the U-shaped configuration of the second jaw.

15. The apparatus of claim 13, wherein the first jaw comprises a flange having a ramped interface, wherein the second jaw comprises an aperture corresponding to the ramped interface, wherein the ramped interface on the first jaw and the aperture on the second jaw are in contact in a needle grasping position.

16. The apparatus of claim 1, wherein the first and second needle grasping members are cooperatively configured to protect a tip portion of the suture needle while providing visibility of the tip portion of the suture needle.

17. An apparatus, comprising:
(a) a shaft, wherein the shaft has a distal end; and
(b) an end effector located at the distal end of the shaft, wherein the end effector comprises a first needle grasping arm, wherein the first needle grasping arm comprises:
  (i) a first needle grasping member, wherein the first needle grasping member comprises sloped surfaces on a side that receives a needle, wherein the first needle grasping member comprises a plurality of mating surfaces configured to interface with the needle simultaneously, wherein two of the mating surfaces of the plurality of mating surfaces of the first needle grasping member configured to interface with the needle simultaneously are perpendicular relative to each other, wherein the two of the mating surfaces of the plurality of mating surfaces of the first needle grasping member are adjacent to the sloped surfaces, and
  (ii) a second needle grasping member, wherein the second needle grasping member comprises sloped surfaces on a side that receives the needle, wherein the second needle grasping member comprises a plurality of mating surfaces configured to interface with the needle simultaneously, wherein two of the mating surfaces of the plurality of mating surfaces of the second needle grasping member configured to interface with the needle simultaneously are perpendicular relative to each other, wherein the two of the mating surfaces of the plurality of mating surfaces of the second needle grasping member are adjacent to the sloped surfaces, wherein the second needle grasping member comprises a location feature,
  wherein the first and second needle grasping members are operable to translate in opposite directions relative to one another to cooperatively align, grasp, and release a suture needle.

18. An apparatus, comprising:
(a) a shaft, wherein the shaft has a distal end;
(b) a needle extending along an arcuate length, wherein the needle comprises:
  (i) a first flat side,
  (ii) a top edge where a portion of the first flat side is perpendicular to an adjacent portion of the top edge,
  (iii) a second flat side parallel to the first flat side, where a portion of the top edge is perpendicular to an adjacent portion of the second flat side, and
  (iv) a bottom edge parallel with the top edge; and
(c) an end effector located at the distal end of the shaft, wherein the end effector comprises a first needle grasping arm, wherein the first needle grasping arm comprises:
  (i) a first needle grasping member, wherein the first needle grasping member comprises a first needle receiving side, a first needle grasping side, and a first needle exit side, wherein the first needle grasping side comprises:
    (A) a first wall, and
    (B) a second wall perpendicular to the first wall, and
  (ii) a second needle grasping member, wherein the second needle grasping member comprises a second needle receiving side, a second needle grasping side, and a second needle exit side, wherein the second needle grasping side comprises:
    (A) a third wall parallel with the first wall, and
    (B) a fourth wall perpendicular to the third wall,
  wherein the first and second needle grasping members are configured to actuate from an open position to a closed position along a first axis, wherein the first needle grasping side and the second needle grasping side are configured to actuate the needle relative to the first and second needle grasping sides along a second axis while the first and second needle grasping members actuate from the open position to the closed position, wherein the second axis is perpendicular with the first axis, wherein the first and second needle grasping members are operable to cooperatively grasp the needle while the first and second needle grasping members are in the closed position, wherein the first wall is configured to abut against the first flat side of the needle while grasping the needle in the closed position, wherein the second wall is configured to abut against the top edge of the needle while grasping the needle in the closed position, wherein the third wall is configured to abut against the second flat side of the needle while grasping the needle in the closed position, wherein the fourth wall is configured to abut against the bottom edge of the needle while grasping the needle in the closed position.

19. An apparatus, comprising:
(a) a shaft defining a longitudinal axis, wherein the shaft has a distal end; and
(b) an end effector located at the distal end of the shaft, wherein the end effector comprises a first needle grasping arm, wherein the first needle grasping arm comprises:
  (i) a first needle grasping member, wherein the first needle grasping member has a needle receiving side, and
  (ii) a second needle grasping member, wherein the second needle grasping member has a needle receiving side,
  wherein the first and second needle grasping members are operable to cooperatively align a suture needle along an arc path by positioning the suture needle about a roll axis, a pitch axis, and a yaw axis, wherein the arc path defines a first plane;

wherein the first and second needle grasping members are further operable to correct at least some deviations of the suture needle about the roll axis, pitch axis, and yaw axis;

wherein the first needle grasping member further comprises surfaces that are configured to interface with surfaces of the suture needle to rotate the suture needle relative to the first needle grasping member as the first and second needle grasping members translate toward each other;

wherein the first needle grasping member comprises a linearly movable first jaw having a first U-shaped configuration having a first U-shaped profile taken along a second plane that is both perpendicular to the first plane and parallel to the longitudinal axis, wherein the first U-shaped configuration comprises a first overlapping portion, wherein the first needle grasping member further comprises a linearly movable second jaw having a second U-shaped configuration having a second U-shaped profile taken along the second plane, wherein the second U-shaped configuration comprises a second overlapping portion, wherein the first overlapping portion of the first U-shaped configuration of the first jaw is configured to overlap with the second overlapping portion of the second U-shaped configuration of the second jaw thereby actuating the suture needle in a vertical direction relative to the U-shaped configuration of both the first jaw and the second jaw, wherein the U-shaped configurations of the first jaw and the second jaw are linearly movable in opposing directions along a common axis;

wherein the first and second needle grasping members are operable to cooperatively grasp and release the suture needle; and wherein the shaft and the end effector are dimensioned to fit through a surgical trocar.

* * * * *